(12) United States Patent
Yilmaz et al.

(10) Patent No.: US 11,350,965 B2
(45) Date of Patent: Jun. 7, 2022

(54) METHODS AND SYSTEMS FOR PERFORMING NAVIGATION-ASSISTED MEDICAL PROCEDURES

(71) Applicant: Ohio State Innovation Foundation, Columbus, OH (US)

(72) Inventors: Alper Yilmaz, Lewis Center, OH (US); Edward W. Martin, Delaware, OH (US); Stephen P. Povoski, Dublin, OH (US); Charles L. Hitchcock, Upper Arlington, OH (US); Enver Ozer, Columbus, OH (US); Ronald Xu, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 290 days.

(21) Appl. No.: 16/459,995

(22) Filed: Jul. 2, 2019

(65) Prior Publication Data
US 2019/0321065 A1    Oct. 24, 2019

Related U.S. Application Data

(62) Division of application No. 14/549,258, filed on Nov. 20, 2014, now Pat. No. 10,383,654.

(51) Int. Cl.
*A61B 34/20* (2016.01)
*A61B 17/3211* (2006.01)
(Continued)

(52) U.S. Cl.
CPC ............ *A61B 17/3211* (2013.01); *A61B 5/06* (2013.01); *A61B 6/12* (2013.01); *A61B 6/462* (2013.01);
(Continued)

(58) Field of Classification Search
CPC .......... A61B 17/3211; A61B 2010/045; A61B 2017/00115; A61B 2017/008;
(Continued)

(56) References Cited

U.S. PATENT DOCUMENTS

| 8,417,006 B2 | 4/2013 | Adams et al. |
| 2012/0182403 A1 | 7/2012 | Lange |

(Continued)

OTHER PUBLICATIONS

Comaniciu, D., et al., "Image-guided decision support system for pathology," Machine Vision and Applications, vol. 11, 1999, pp. 213-224.

(Continued)

*Primary Examiner* — Mark D Remaly
(74) *Attorney, Agent, or Firm* — Meunier Carlin & Curfman LLC

(57) ABSTRACT

Systems and methods are described for performing navigation-assisted medical procedures such as biopsies, surgeries and pathology procedures by obtaining location information of an item of interest located within at least a portion of a subject; sensing position information of a moveable device; determining a relative position of the moveable device to the item of interest using the location information of the item of interest and the position information of the moveable device; and providing feedback based on the relative position of the moveable device to the item of interest that can be used to change the relative position of the moveable device to the item of interest.

13 Claims, 27 Drawing Sheets

(51) Int. Cl.

| | |
|---|---|
| *B25J 9/16* | (2006.01) |
| *A61B 34/30* | (2016.01) |
| *A61B 34/00* | (2016.01) |
| *A61B 5/06* | (2006.01) |
| *A61B 6/12* | (2006.01) |
| *A61B 6/00* | (2006.01) |
| *A61B 10/04* | (2006.01) |
| *A61B 17/00* | (2006.01) |
| *A61B 90/11* | (2016.01) |
| *A61B 90/00* | (2016.01) |
| *A61B 90/50* | (2016.01) |
| *A61B 5/00* | (2006.01) |
| *A61B 5/055* | (2006.01) |
| *A61B 6/03* | (2006.01) |

(52) U.S. Cl.
CPC .............. *A61B 6/466* (2013.01); *A61B 6/502* (2013.01); *A61B 6/5235* (2013.01); *A61B 34/20* (2016.02); *A61B 34/30* (2016.02); *A61B 34/76* (2016.02); *B25J 9/1664* (2013.01); *B25J 9/1694* (2013.01); *A61B 5/0077* (2013.01); *A61B 5/055* (2013.01); *A61B 5/062* (2013.01); *A61B 5/067* (2013.01); *A61B 6/032* (2013.01); *A61B 6/037* (2013.01); *A61B 6/4258* (2013.01); *A61B 90/11* (2016.02); *A61B 2010/045* (2013.01); *A61B 2017/008* (2013.01); *A61B 2017/00115* (2013.01); *A61B 2034/2048* (2016.02); *A61B 2034/2057* (2016.02); *A61B 2034/301* (2016.02); *A61B 2090/374* (2016.02); *A61B 2090/3762* (2016.02); *A61B 2090/392* (2016.02); *A61B 2090/3908* (2016.02); *A61B 2090/502* (2016.02); *G05B 2219/40121* (2013.01); *G05B 2219/40131* (2013.01); *Y10S 901/09* (2013.01)

(58) Field of Classification Search
CPC .... A61B 2034/2048; A61B 2034/2057; A61B 2034/301; A61B 2090/374; A61B 2090/3762; A61B 2090/3908; A61B 2090/392; A61B 2090/502; A61B 34/20; A61B 34/30; A61B 34/76; A61B 5/0077; A61B 5/055; A61B 5/06; A61B 5/062; A61B 5/067; A61B 6/032; A61B 6/037; A61B 6/12; A61B 6/4258; A61B 6/462; A61B 6/466; A61B 6/502; A61B 6/5235; A61B 90/11; B25J 9/1664; B25J 9/1694; G05B 2219/40121; G05B 2219/40131; Y10S 901/09

See application file for complete search history.

(56) References Cited

U.S. PATENT DOCUMENTS

| | | |
|---|---|---|
| 2013/0172902 A1 | 7/2013 | Lightcap |
| 2013/0197357 A1 | 8/2013 | Green |
| 2013/0243302 A1 | 9/2013 | Liu et al. |
| 2016/0051164 A1 | 2/2016 | Derichs et al. |

OTHER PUBLICATIONS

Parikh, J., et al., "Image-Guided Tissue Sampling: Where Radiology Meets Pathology," The Breast Journal, vol. 11, No. 6, 2005, pp. 403-409.

Robboy, S.J., et al., "Pathologist Workforce in the United States: I. Development of a Predictive Model to Examine Factors Influencing Supply," Archives of Pathology & Laboratory Medicine, vol. 137, No. 12, 2013, pp. 1723-1732.

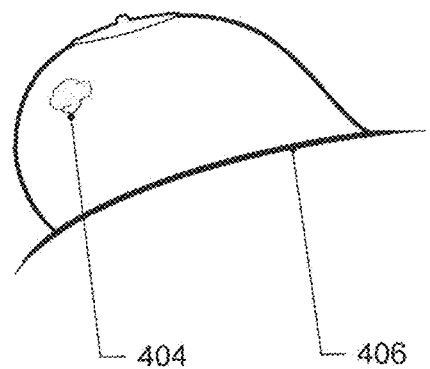
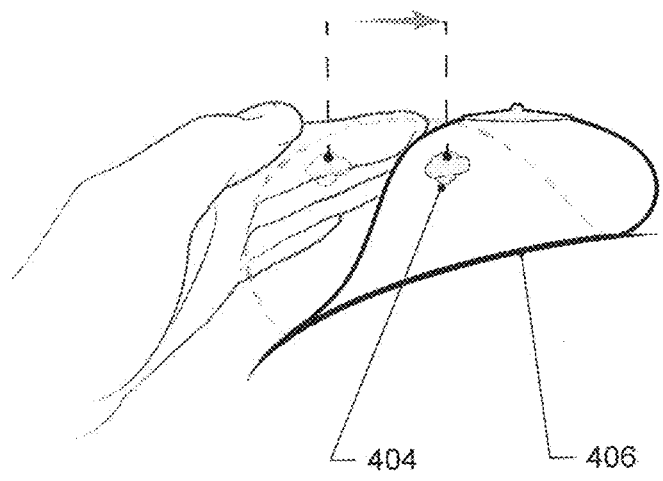
FIG. 4A
FIG. 4B

METHODS AND SYSTEMS FOR PERFORMING NAVIGATION-ASSISTED MEDICAL PROCEDURES

CROSS-REFERENCE TO RELATED APPLICATION

This application is a divisional application of U.S. patent application Ser. No. 14/549,258 filed Nov. 20, 2014 (PG-Publication No.: US 2016/0143693 A1, published May 26, 2016), which is fully incorporated by reference and made a part hereof.

BACKGROUND

When performing medical procedures such as surgery, obtaining pathological samples, biopsies, and the like, medical personnel still use methods such as palpation, sight and static two-dimensional imaging to locate and sample or review items of interest when performing such procedures. Such reliance upon the skill and experience of the medical personnel and dimensionally-limited imaging of the item of interest may result in reduced quality and accuracy of the medical procedure. For example, pathologic staging of solid tumors involves determining the presence and extent of disease. Precise specimen processing is desired for establishing patient customized management plans that may indicate the need for post-operative chemotherapy and/or radiation therapy. Failure to identify malignant involvement in tissues can lead to the misdiagnosis and mismanagement of patients, leading to undesirable outcomes. Furthermore, correctly determining the extent of disease involves accurate assessment of the tumor's size, and the presence or absence of metastatic disease involving lymph nodes and distant tissues. Hence, the pathologist's assessment is crucial, and it plays a key role in basing future treatment options for patients.

Similarly, surgery has offered the best opportunity of a cure for patients with solid malignancies. Furthermore, the best surgery is the first surgery. Optimal surgical approaches to cancer resection in the past were limited to visual and tactile cues in identifying the tumor's location and extent. Surgical procedures were based upon surgical anatomy and traditional planes of resection that cancer cells disregard. Hence, it is desirable that the surgical team "see" all of the tumor(s), including metastases, to achieve the best resection and offer the patient the best possible outcome.

Likewise, biopsies such as fine needle biopsies are performed predominately using the medical personnel's sense of sight and feeling. Biopsies may be inaccurate or incorrect when the needle or other biopsy instrument extends through the item of interest and unaffected tissue obtained.

Other forms of medical procedures and surgeries such as, for example, reconstructive surgeries that involve bone replacement also have predominately relied upon the sight and feel of the surgeon, which could result in painful mis-alignment and the need for additional surgeries.

It can be said that a surgeon is as good as his or her tools. Unfortunately, though, because of the reliance upon the sight and feel of the medical professional, it has been found that in cancer surgery up to 50 percent of all resections that residual tumor has been left behind. It can take some amount of time for the residual tumor to become medically symptomatic. In pathology, even with slice depths of only two to five millimeters (mm), staging can be incorrect up to 30 percent of all cases. And, with reconstructive surgery, bone implants can be misaligned in over 50 percent of all surgeries. Therefore, what are needed are systems and methods that overcome challenges in the art, some of which are described above.

SUMMARY

In one aspect, a method of performing navigation-assisted medical procedures is described. One embodiment of the method comprises obtaining location information of an item of interest located within at least a portion of a subject; sensing position information of a moveable device; determining a relative position of the moveable device to the item of interest using the location information of the item of interest and the position information of the moveable device; and providing feedback based on the relative position of the moveable device to the item of interest that can be used to change the relative position of the moveable device to the item of interest. Location information for the item of interest can be obtained pre-operative and intra-operative.

Alternatively or optionally, obtaining location information of the item of interest can comprise obtaining an image of at least a portion of the item of interest.

Alternatively or optionally, obtaining an image of at least a portion of the item of interest can comprise obtaining a three-dimensional image of at least a portion of the item of interest, which can comprise obtaining the three-dimensional image of at least a portion of the item of interest using a targeted imaging technique such as one or more of PET/CT, SPECT/CT, PET MRI, ultrasound, florescence, and the like.

Alternatively or optionally, the targeted imaging technique can comprise injecting a material into the item of interest or the subject and obtaining a three-dimensional image of at least a portion of the item of interest using one or more cameras that detect the injected material. The injected materials comprise one or more of Technetium-99, F18, zirconium 89, iodine 123, iodine 124, iodine 125, iodine 131, copper 64, gallium 67, gallium 68, lutetium 177, xenon 133, indium 111, and the like.

Alternatively or optionally, obtaining a three-dimensional image of at least a portion of the item of interest can comprise obtaining the three-dimensional image of at least a portion of the item of interest using a non-targeted imaging technique such as one or more of X-Ray, ultrasound, CT, ultrasound, MRI, and the like.

Alternatively or optionally, obtaining location information of an item of interest located within at least a portion of a subject can comprise obtaining location information of a tumor within at least a portion of a subject, cancerous tissue within at least a portion of a subject, an organ within a body of the subject, and the like.

Alternatively or optionally, obtaining location information of an item of interest located within at least a portion of a subject can comprise obtaining location information of the item of interest within a body of the subject, location information of the item of interest within an organ of the subject, or location information of the item of interest within a tissue specimen. The organ can contained within a body of the subject, or it can be removed from a body of the subject.

Alternatively or optionally, one embodiment of the method can further comprise inserting the moveable device into the item of interest, wherein the feedback indicates a depth that the moveable device has been inserted into the item of interest.

Alternatively or optionally, providing feedback based on the relative position of the moveable device to the item of interest that can be used to change the relative position of the moveable device to the item of interest further comprises acquiring a real-time image of the at least a portion of the subject, wherein the acquired real-time image is referenced to the same coordinate system as the location information of the item of interest and the position information of the moveable device; and displaying the real-time image of the at least a portion of the subject further comprising the location information of the item of interest and the position information of the moveable device super-imposed on the real-time image of the at least a portion of the subject. The feedback can also be audible or haptic feedback.

Alternatively or optionally, acquiring a real-time image of the at least a portion of the subject can comprise acquiring the real-time image using at least a pair of stereo electro-optical cameras.

Alternatively or optionally, referencing the acquired real-time image to the same coordinate system as the location information of the item of interest and the position information of the moveable device comprises placing one or more fiducials on or around the at least a portion of the subject. At least one of the one or more fiducials comprise a radioactive fiducial.

Alternatively or optionally, displaying the real-time image of the at least a portion of the subject further comprising the location information of the item of interest and the position information of the moveable device super-imposed on the real-time image of the at least a portion of the subject can comprise displaying the real-time image of the at least a portion of the subject further comprising the location information of the item of interest and the position information of the moveable device super-imposed on the real-time image of the at least a portion of the subject on a display that is visible to a person that is moving the moveable device.

Alternatively or optionally, the real-time image of the at least a portion of the subject can further comprise the location information of the item of interest and the position information of the moveable device super-imposed on the real-time image of the at least a portion of the subject is displayed to the person using augmented reality glasses that are worn by the person.

Alternatively or optionally, providing feedback based on the relative position of the moveable device to the item of interest that can be used to change the relative position of the moveable device to the item of interest comprises providing one or more of visual, audible or haptic feedback that is used to move the moveable device closer to the item of interest. For example, audible feedback can comprise computer-generated voice commands, computer-generated noises that change as the moveable device moves closer to or further away from the item of interest, and the like.

Alternatively or optionally, providing feedback based on the relative position of the moveable device to the item of interest that can be used to change the relative position of the moveable device to the item of interest can comprise providing a control signal that is used to provide robotic control of the moveable device.

Alternatively or optionally, sensing position information of the moveable device comprises actively or passively sensing position information of a biopsy needle, a scalpel, a pathology wand, a locator wand, a bone segment, and the like.

Alternatively or optionally, sensing position information of the moveable device can comprise obtaining position information using a three-dimensional sensor. For example, the three-dimensional sensor can be located on at least one of the moveable device, eyeglasses of a person in view of the moveable device, or anywhere the three-dimensional sensor can sense the moveable device. In one embodiment, the eyeglasses comprise augmented reality eyeglasses.

Alternatively or optionally, determining the relative position of the moveable device to the item of interest using the location information of the item of interest and the position information of the moveable device can be performed using a computing device.

Alternatively or optionally, one embodiment of the method can further comprising re-registration of the location information of the item of interest located within at least a portion of a subject. For example, re-registration can occur after movement of the item of interest, the at least a portion of the subject, or the subject or after removal of at least a portion of the item of interest from the at least a portion of the subject.

Alternatively or optionally, re-registration can occur dynamically.

Alternatively or optionally, one embodiment of the method can further comprise estimating movement or deformation of the item of interest caused by movement or palpation of the at least a portion of the subject, wherein the location information of the item of interest is modified by the estimate.

Alternatively or additionally, movement of the item of interest within the at least a portion of a subject can be modeled using a soft tissue motion engine and the location information of the item of interested can be updated using the modeled information. The movement can be caused by palpation of the at least a portion of a subject or a change in position of the subject.

In another aspect, a system for performing navigation-assisted medical procedures is described. One embodiment of the system comprises a device that obtains location information of an item of interest located within at least a portion of a subject; a sensor that senses position information of a moveable device; and a computing device that receives the location information of the item of interest from the device and the position information of the moveable device and executes computer-readable instructions that determine a relative position of the moveable device to the item of interest using the location information of the item of interest and the position information of the moveable device and provides feedback based on the relative position of the moveable device to the item of interest that can be used to change the relative position of the moveable device to the item of interest.

For example, the device that obtains location information of an item of interest located within at least a portion of a subject can comprise one or more of a PET/CT scanner, a SPECT/CT camera, a PET MRI system, a florescence detection system, an X-Ray system, an ultrasound scanner, a CT, an MRI, and the like. The item of interest can be one or more of a tumor within at least a portion of a subject, cancerous tissue within at least a portion of a subject, a tissue sample of the subject, an organ within a body of the subject, a section of bone for bone replacement surgery, and the like. In one embodiment, the moveable device is inserted into the item of interest and the computing device provides feedback that indicates a depth that the moveable device has been inserted into the item of interest.

One embodiment of the system further comprises one or more cameras in communication with the computing device. The cameras acquire a real-time image of the at least a portion of the subject, wherein the acquired real-time image is referenced to the same coordinate system as the location information of the item of interest and the position information of the moveable device. A display in communication with the computing device displays the real-time image of the at least a portion of the subject and the location information of the item of interest and the position information of the moveable device is super-imposed on the real-time image of the at least a portion of the subject on the display. The display can comprise augmented reality glasses.

It should be understood that the above-described subject matter may also be implemented as a computer-controlled apparatus, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIGS. 4A and 4B illustrate deformation of the portion of a subject and movement or deformation of the item of interest located within the portion of a subject.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

Figure 1:
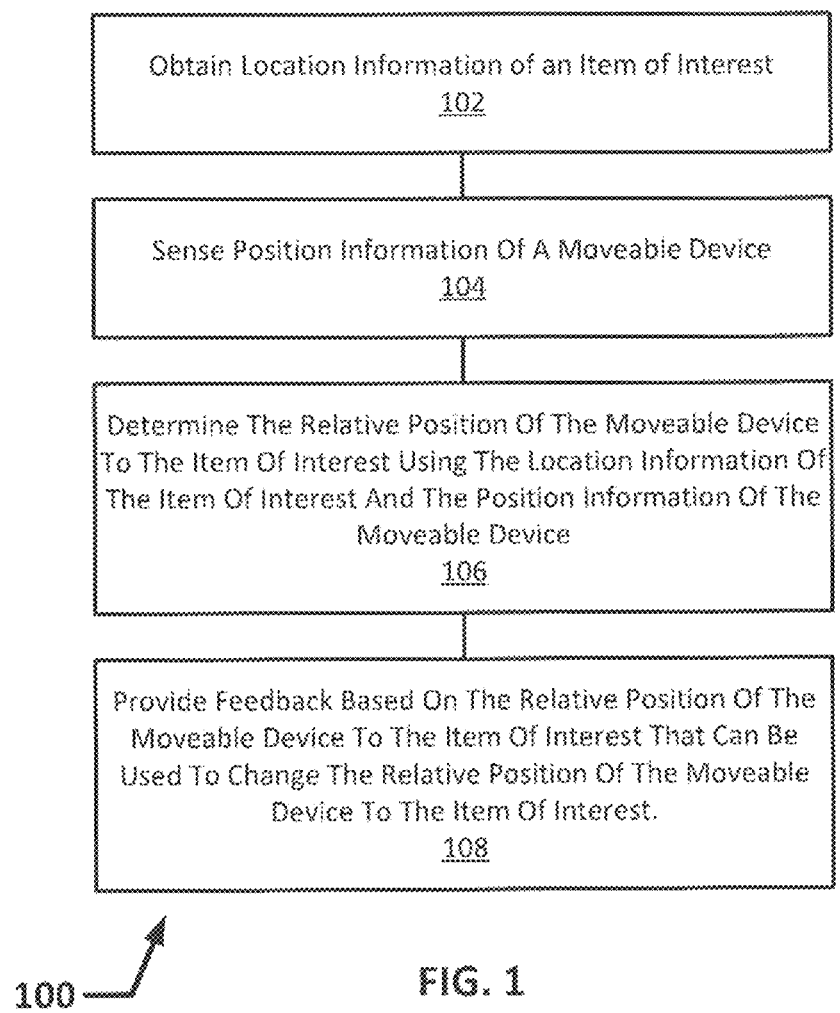
FIG. 1 is a flow diagram illustrating example operations for performing navigation-assisted medical procedures.

Referring now to FIG. 1, example methods of performing navigation-assisted medical procedures are described. It should be understood that the navigation-assisted medical procedures can be at least partially performed by at least one processor (described below). Additionally, the navigation-assisted medical procedures can optionally be implemented within a cloud computing environment, for example, in order to decrease the time needed to perform the algorithms, which can facilitate visualization of the prior analysis on real-time images. Cloud computing is well-known in the art. Cloud computing enables network access to a shared pool of configurable computing resources (e.g., networks, servers, storage, applications, and services) that can be provisioned and released with minimal interaction. It promotes high availability, on-demand self-services, broad network access, resource pooling and rapid elasticity. It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Referring now to FIG. 1, a flow diagram illustrating example operations 100 for performing navigation-assisted medical procedures is shown. At step 102 location information of an item of interest located within at least a portion of a subject is obtained. For example, obtaining location information of the item of interest can comprise obtaining an image of at least a portion of the item of interest such as a two-dimensional (2D) or a three-dimensional (3D) image. In one aspect, obtaining a three-dimensional image of at least a portion of the item of interest comprises obtaining the three-dimensional image using a targeted imaging technique. Such targeted techniques can include using one or more of Positron Emission Tomography/Computed Tomography (PET/CT), Single Photon Emission Computed Tomography/Computed Tomography (SPECT/CT), Positron Emission Tomography Magnetic Resonance Imaging (PET MRI), fluorescence spectroscopy, and the like. In various embodiments, the targeted imaging techniques can comprise injecting the subject with a material and obtaining a three-dimensional image of at least a portion of the item of interest using one or more cameras that detect the injected material. For example, the injected materials can comprise one or more of Technetium-99, F18, zirconium 89, iodine 123, iodine 124, iodine 125, copper 64, gallium 67, gallium 68, lutetium 177, xenon 133, indium 111, and the like. In other aspects, obtaining a three-dimensional image of at least a portion of the item of interest comprises obtaining the three-dimensional image of at least a portion of the item of interest using a non-targeted imaging technique. For example, the non-targeted imaging techniques can include using one or more of X-Ray, ultrasound, CT, MRI, and the like. The item of interest can be any tissue, organ, growth or abnormality, bone section, and the like. For example, obtaining location information of an item of interest located within at least a portion of a subject can comprise obtaining location information of a tumor within at least a portion of a subject, cancerous tissue within at least a portion of a subject, an organ within a body of the subject, a bone section used in bone transplant surgery, and the like. In one aspect, obtaining location information of an item of interest located within at least a portion of a subject comprises obtaining location information of the item of interest within a body of the subject, location information of the item of interest within an organ of the subject, location information of the item of interest within a tissue specimen, and the like. For example, when obtaining location information of the item of interest within an organ of the subject, the organ may be contained within a body of the subject (e.g., when performing a biopsy or surgery), or the organ may have been removed from a body of the subject (e.g., pathology).

At step 104 of an exemplary method of performing a navigation-assisted medical procedure, position information of a moveable device is sensed. Such sensing may active or passive sensing. In various embodiments, the moveable device can comprise a biopsy needle, a scalpel, a pathology wand, a locator wand, and the like. Alternatively or additionally, the moveable device can be a bone section that is being aligned with or in a bone transplant surgery. In one aspect, the position information of the moveable device is sensed using a three-dimensional sensor. For example, a Kinect™ (Microsoft Corporation) or Kinect™-type depth sensor can be used to obtain the position information of the moveable device. In other instances, one or more cameras (infrared or visible), accelerometers, gyroscopes, and the like can be used to obtain location information of the moveable device. In various aspects, the three-dimensional sensor is located on at least one of the moveable device, eyeglasses of a person in view of the moveable device, or anywhere the three-dimensional sensor can sense the moveable device. In one aspect, the three-dimensional sensor for obtaining location information of the moveable device can be located on augmented reality eyeglasses such as, for example, Google Glass™.

At step 106, a relative position of the moveable device to the item of interest can be determined using the location information of the item of interest and the position information of the moveable device. Determining the relative position of the moveable device to the item of interest using the location information of the item of interest and the position information of the moveable device can be at least partially performed using one or more computing devices, such as the one described herein.

At step 108, feedback is provided based on the relative position of the moveable device to the item of interest that can be used to change the relative position of the moveable device to the item of interest. In various aspects, providing feedback based on the relative position of the moveable device to the item of interest that can be used to change the relative position of the moveable device to the item of interest can comprise acquiring a real-time image of the at least a portion of the subject, wherein the acquired real-time image is referenced to the same coordinate system as the location information of the item of interest and the position information of the moveable device; and displaying the real-time image of the at least a portion of the subject further comprising the location information of the item of interest and the position information of the moveable device superimposed on the real-time image of the at least a portion of the subject. For example, in one embodiment acquiring a real-time image of the at least a portion of the subject can be performed using at least a pair of stereo electro-optical cameras. Referencing the real-time image to the same coordinate system as the location information of the item of interest and the position information of the moveable device can comprise placing one or more fiducials on or around the at least a portion of the subject. In one aspect, the fiducials can comprise visual markers that can be detected by the cameras. In other aspects, the fiducials can be radioactive markers or other non-visual markers that can not only be detected by the cameras but also be detected by PET/CT, SPECT/CT, PET MRI, fluorescence spectroscopy, and the like so that location information of the item of interest can be obtained either continuously while the moveable device is being position in reference to the item of interest or on an interment basis and the location information of the item of interest and the real-time image can be reference to the same coordinate system. In one aspect, the fiducials comprise both, visual and non-visual markers. Generally, the real-time image of the at least a portion of the subject further comprising the location information of the item of interest and the position information of the moveable device superimposed on the real-time image of the at least a portion of the subject will be displayed on a display that is visible to a person that is moving the moveable device. For example, in one aspect, the position information of the moveable device super-imposed on the real-time image of the at least a portion of the subject is displayed to the person using augmented reality glasses that are worn by the person. Providing feedback can, in some embodiments, comprise providing audible or haptic feedback that is used to move the moveable device closer to the item of interest. For example, the audible feedback may comprise computer-generated voice commands. In one aspect, the audible feedback comprises computer-generated noises that change as the moveable device moves closer to or further away from the item of interest. For example, the noise may get louder as the movable device gets closer to the item of interest, or it may get quieter. Similarly, a series of clicks may get more frequent and or louder as the movable device gets closer to the item of interest, or vice versa. These are only examples of feedback that can be provided based upon the movement of the moveable device relative to the item of interest and it is to be appreciated that any form of feedback is contemplated in embodiments of this invention. In one embodiment, the feedback based on the relative position of the moveable device to the item of interest that can be used to change the relative position of the moveable device to the item of interest comprises providing a control signal that is used to provide robotic control of the moveable device; alternatively this can be used as a vocal comment to the person holding the movable device. Using the method described above, the moveable device (e.g., biopsy needle, pathology wand, scalpel, bone section, etc.) can be inserted into the item of interest, wherein the feedback can provide an indication of a depth and position that the moveable device has been inserted into the item of interest.

Figure 2:
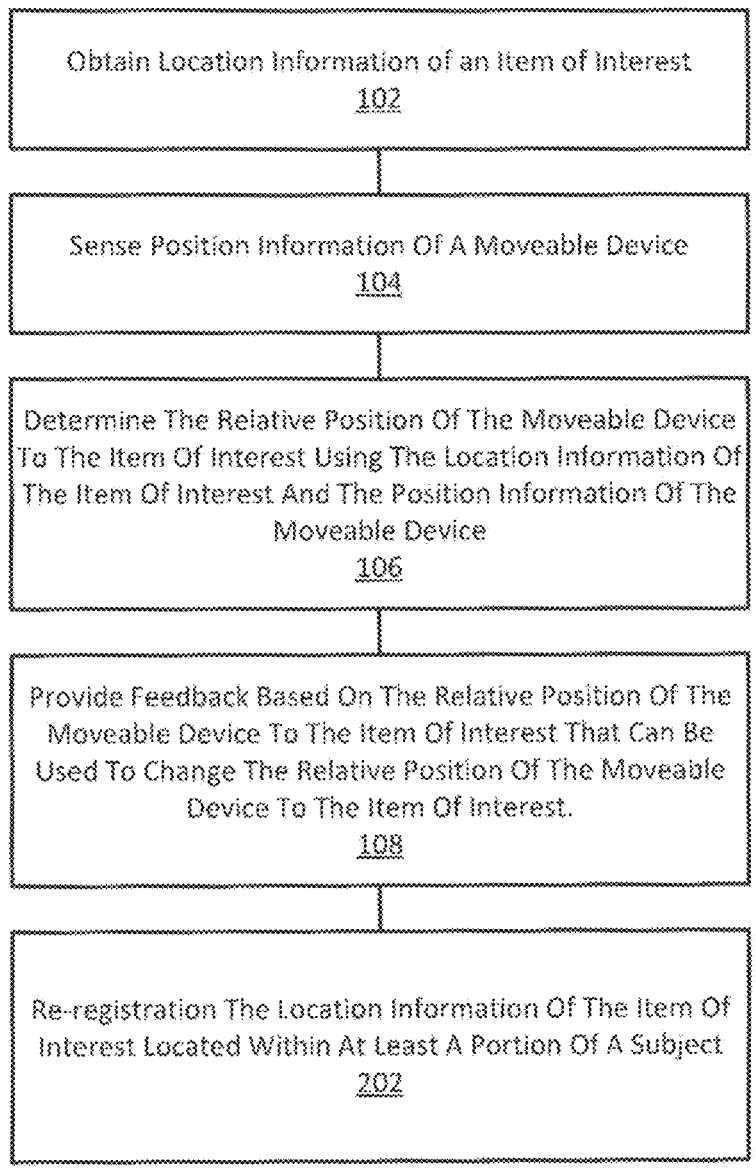
FIG. 2 is another flow diagram illustrating example operations for performing navigation-assisted medical procedures.

Referring now to FIG. 2, a flow diagram illustrating example operations 200 for performing navigation-assisted medical procedures is shown. This exemplary process 200 includes the steps of flow chart 100, above, but further includes the step (step 202) of re-registration of the location information of the item of interest located within at least a portion of a subject. This step comprises obtaining location information of the items of interest either during or after a procedure involving the moveable device. Re-registration can be performed using the same devices and techniques as described in step 102, above, to initially determine the location of the item of interest. Re-registration may occur after movement of the item of interest, the at least a portion of the subject, or the subject, after removal of at least a portion of the item of interest from the at least a portion of the subject, and the like. For example, if the item of interest is cancerous tissue and the movable device is a scalpel, the surgeon may want to re-register the item of interest after the initial surgical procedure to make sure that all of the cancerous tissue has been removed. In one aspect, re-registration occurs dynamically while the medical procedure is being performed.

Figure 3:
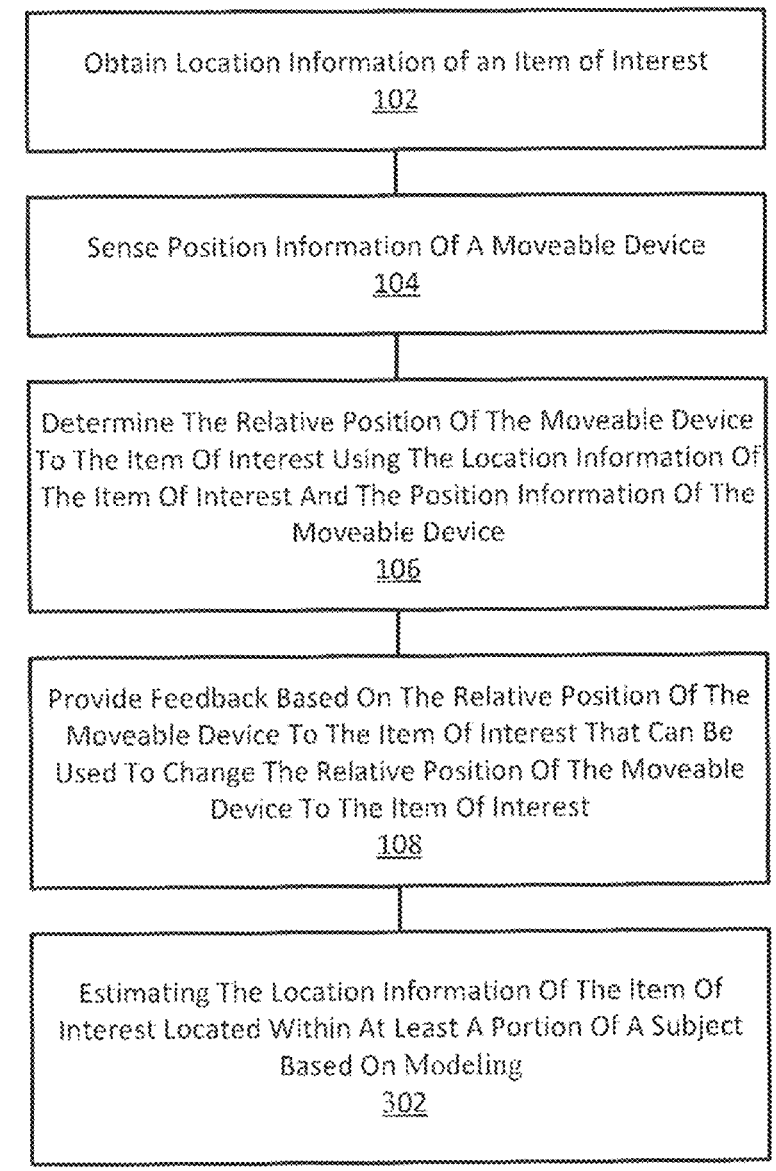
FIG. 3 illustrates yet another embodiment of a flow diagram illustrating example operations for performing navigation-assisted medical procedures.

FIG. 3 illustrates yet another embodiment of a flow diagram illustrating example operations 300 for performing navigation-assisted medical procedures. This exemplary process 300 includes the steps of flow chart 100, above, but further includes the step (step 302) of estimating the location information of the item of interest located within at least a portion of a subject based on modeling the at least a portion of a subject and using an algorithmic deformation model to handle the unobserved motion within the body of the subject. Such movement of the item of interest may be cause by palpation, movement, repositioning of the subject or the at least a portion of a subject and the like. For example, as shown in FIGS. 4A and 4B, location information of the item of interest 404 located within at least a portion of a subject 406 is initially obtained (see FIG. 4A). In FIG. 4B, the same portion of the subject 406 undergoes deformation or movement. Such deformation or movement causes movement and possibly deformation of the item of interest 404 within the portion of the subject 406.

Figure 5:
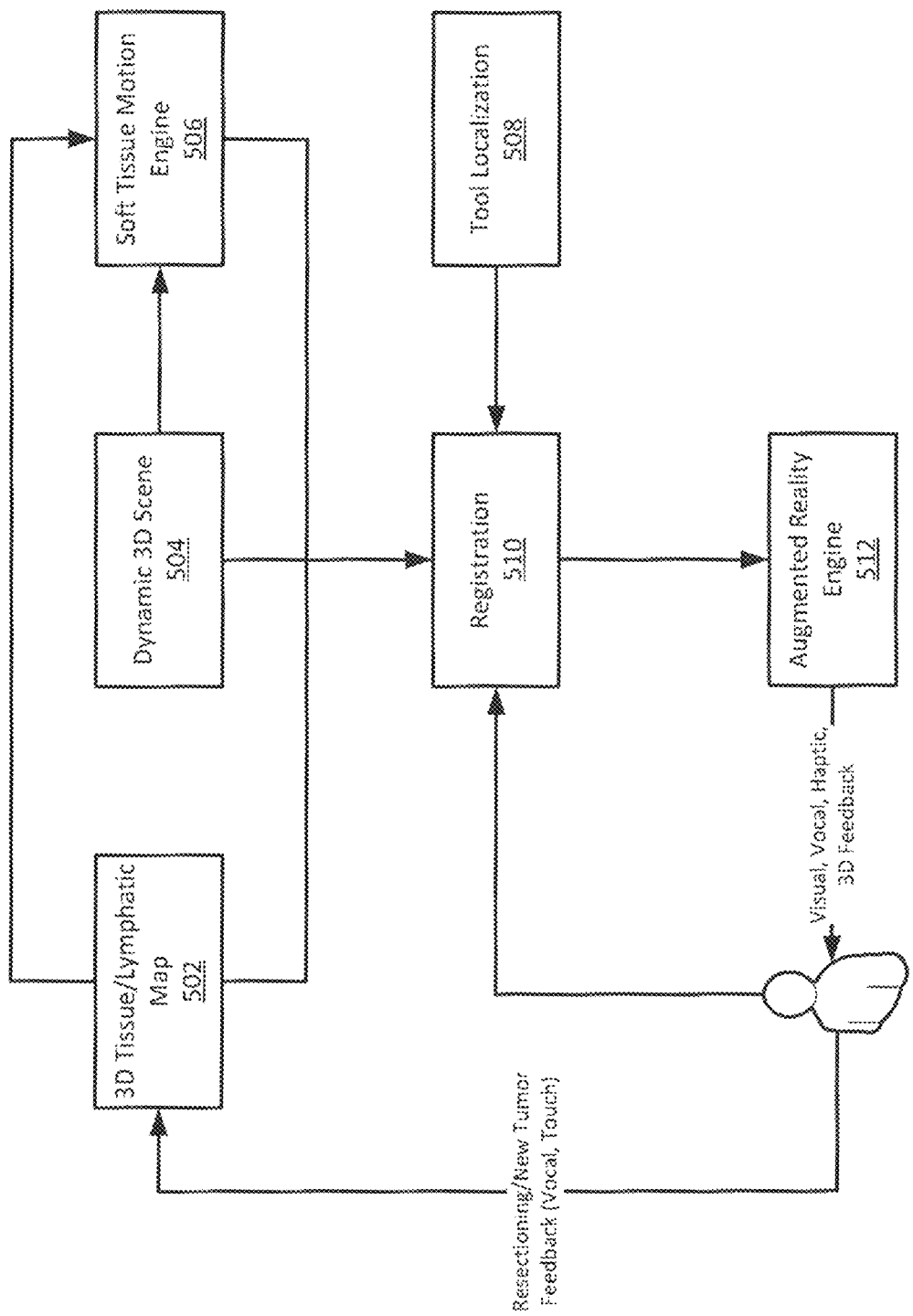
FIG. 5 illustrates an exemplary process diagram according to embodiments of the present invention.

FIG. 5 illustrates an exemplary process diagram according to embodiments of the present invention. As shown in the process diagram, a 3D tissue or lymphatic map 502 can be created; a dynamic 3D scene is also developed (step 504); a soft tissue motion engine (506) can be used to estimate how the item of interest moves or deforms within at least a portion of the subject; tool localization (508) comprises tracking the location of the wand, scalpel, biopsy needle, bone segment, and the like; registration (510) involves bringing the 3D tissue or lymphatic map, the 3D scene, estimation location changes for the item of interest and the tool localization together to provide to an augmented reality engine 512, which can visual, vocal, haptic, 3D and the like feedback to the professional 514 performing the procedure. The professional can also provide information about any tumors or other items of interest back discovered while performing the procedure to the 3D map so that the procedure can be optimized thereby requiring fewer follow-on procedures.

3D tissue or lymphatic map creation at step 502 can involve one or more of targeted or non-targeted preoperative imaging; marking of an item of interest and 3D map generation. Targeted or non-targeted imaging can comprise CT, MRI, PET/CT, SPECT/CT, ultrasound, and the like. Marking of the item of interest can comprise marking the item of interest using, for example, radioactive, magnetic, RFID, and the like marker placement on, in or near the item of interest. 3D map generation can involve triangulation of regions, radio frequency (RF) time of flight, and 3D surface modeling using CT, MRI, SPECT/CT, and the like.

Developing a dynamic 3D scene (step 504) can involve depth sensing via infrared imaging using, for example, structured light concept or time of flight principals. Establishing the dynamic 3D scene can also involve static marker (fiducial) placement and tracking using, for example, a static multi-camera setup and real-time detection, tracking and triangulation.

The soft tissue motion engine (506) comprises tissue density models of static 3D tissue, lymphatic map and bone. 3D surface sensing is used to sense movement of the surface of the at least portion of the subject and mathematical models are used to estimate the effect surface motion has on the item of interest. Therefore, an estimate of how the item of interest moves or deforms within at least a portion of the subject can be developed.

Tool localization 508 comprises positioning and orientation estimation of a tool used by a professional such as a wand, scalpel, needle, probe, and the like or can even be used to estimate the location of a bone segment. This can be accomplished in at least two ways—one way comprises tracking and triangulation of visual markers on the tool or bone segment and the other way comprises special tools designed with inertial sensors such as accelerometers, gyroscopes, magnetometer, and the like.

Registration 510, as described above, comprises bringing the 3D tissue or lymphatic map, the 3D scene, estimation location changes for the item of interest and the tool localization together to provide to an augmented reality engine 512 so that the professional can be provided with 3D localization of the item of interest, the scene, etc. The professional can be provided with one or more visual vocal and haptic feedback. Visual feedback can be in the form of, for example, a perspective 3D map projection to goggles or glasses worn by the professional, scene projection of a 3D tissue map via a projector, and the like. Vocal feedback can provide voice or computer generated verbal directions to the professional. Haptic feedback can be multipoint haptic feedback to provide, for example, vibration to denote distance and position of the tool to the item of interest, distance encoded vibration frequency, and the like.

Also, as noted above, the professional can provide feedback during or after the procedure. For example, during cancer surgery the professional can mark new unobserved tumors via radioactive probes or palpation, 3D mapping for the new tumor, or marking resected tissue for 3D map removal. For example, the professional can provide vocal or touch feedback to the system.

Figure 6:
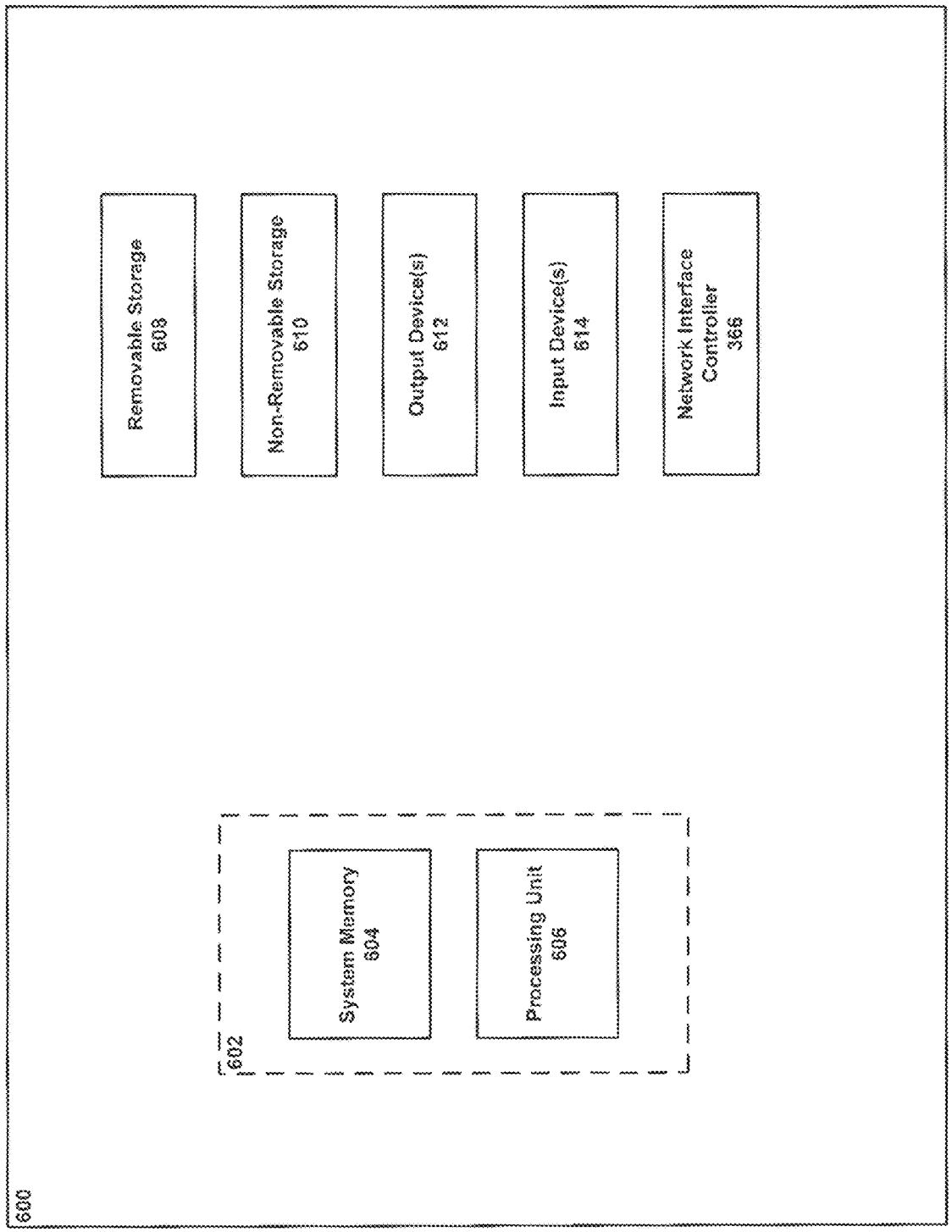
FIG. 6 is a block diagram of an example computing device upon which embodiments of the invention may be implemented.

When the logical operations described herein are implemented in software, the process may execute on any type of computing architecture or platform. For example, referring to FIG. 6, an example computing device upon which embodiments of the invention may be implemented is illustrated. In particular, at least one processing device described above may be a computing device, such as computing device 600 shown in FIG. 6. The computing device 600 may include a bus or other communication mechanism for communicating information among various components of the computing device 600. In its most basic configuration, computing device 600 typically includes at least one processing unit 606 and system memory 604. Depending on the exact configuration and type of computing device, system memory 604 may be volatile (such as random access memory (RAM)), non-volatile (such as read-only memory (ROM), flash memory, etc.), or some combination of the two. This most basic configuration is illustrated in FIG. 6 by dashed line 602. The processing unit 606 may be a standard programmable processor that performs arithmetic and logic operations necessary for operation of the computing device 600.

Computing device 600 may have additional features/functionality. For example, computing device 600 may include additional storage such as removable storage 608 and non-removable storage 610 including, but not limited to, magnetic or optical disks or tapes. Computing device 600 may also contain network connection(s) 616 that allow the device to communicate with other devices. Computing device 600 may also have input device(s) 614 such as a keyboard, mouse, touch screen, etc. Output device(s) 612 such as a display, speakers, printer, etc. may also be included. The additional devices may be connected to the bus in order to facilitate communication of data among the components of the computing device 600. All these devices are well known in the art and need not be discussed at length here.

The processing unit 606 may be configured to execute program code encoded in tangible, computer-readable media. Computer-readable media refers to any media that is capable of providing data that causes the computing device 600 (i.e., a machine) to operate in a particular fashion. Various computer-readable media may be utilized to provide instructions to the processing unit 606 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 606 may execute program code stored in the system memory 604. For example, the bus may carry data to the system memory 604, from which the processing unit 606 receives and executes instructions. The data received by the system memory 604 may optionally be stored on the removable storage 608 or the non-removable storage 610 before or after execution by the processing unit 606.

Computing device 600 typically includes a variety of computer-readable media. Computer-readable media can be any available media that can be accessed by device 600 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 604, removable storage 608, and non-removable storage 610 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 600. Any such computer storage media may be part of computing device 600.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Figure 7:
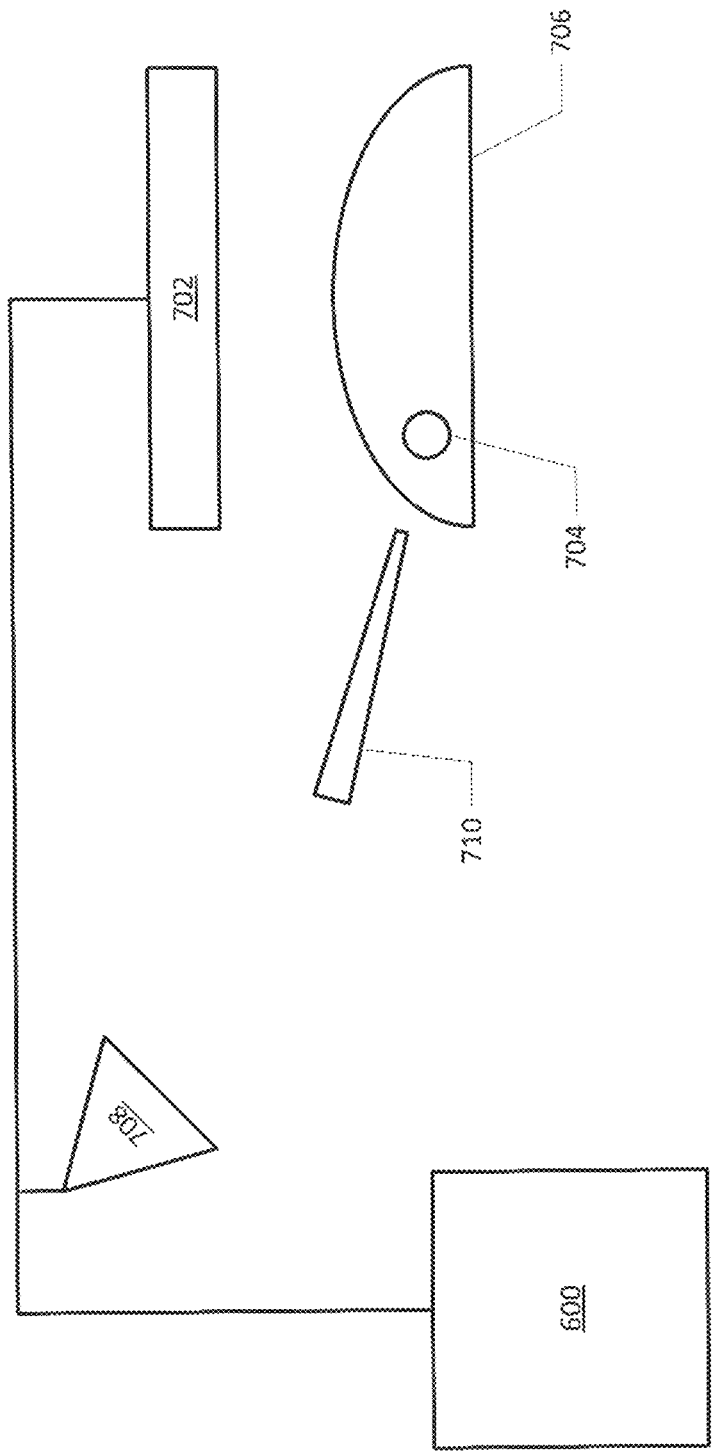
FIG. 7 illustrates an exemplary overview system for performing navigation-assisted medical procedures.

FIG. 7 illustrates an exemplary overview system for performing navigation-assisted medical procedures. In one embodiment, the system comprises a device 702 that obtains location information of an item of interest 704 located within at least a portion of a subject 706. In one aspect, the device 702 that obtains location information of an item of interest 704 located within at least a portion of a subject 706 comprises a device that obtains images using targeted imaging techniques. For example, the device 702 can be one or more of a PET/CT scanner, a SPECT/CT camera, a PET MRI system, a florescence detection system, and the like. In various aspects, the device 702 that obtains images using targeted imaging techniques includes one or more cameras that can detect a material that has been injected into the item of interest or the subject. For example, the device 702 can be a camera, such as a gamma camera, that can detect one or more of Technetium-99, F18, zirconium 89, iodine 123, iodine 124, iodine 125, iodine 131, copper 64, gallium 67, gallium 68, lutetium 177, xenon 133, indium 111, and the like. In other aspects, the device 702 that obtains location information of an item of interest located within at least a portion of a subject can comprise a device that obtains images using non-targeted imaging techniques. For example, the device 702 can be one or more of an X-Ray system, an ultrasound scanner, a CT, an MRI, and the like. The item of interest 704 can be one or more of a tumor within at least a portion of a subject 706, cancerous tissue within at least a portion of a subject 706, a tissue sample of the subject, an organ within a body of the subject, a bone segment for a bone transplant, and the like. For example, the item of interest 704 can be located within a tissue specimen, within a body of the subject, an organ of the subject, and the like. If the item of interest 704 is an organ, the organ may be contained within a body of the subject or the organ may have been removed from a body of the subject.

Further comprising the system of FIG. 7 is a sensor 708 that senses position information of a moveable device 710. The sensor 708 can be an active or a passive sensor. For example, the sensor 708 can be a three-dimensional sensor. For example, a Kinect™(Microsoft Corporation) or Kinect™-type depth sensor can be used to obtain the position information of the moveable device 710. In other instances, the sensor 708 can be one or more cameras (infrared or visible), accelerometers, gyroscopes, and the like that can be used to obtain location information of the moveable device 710. In various embodiments, sensor 708 can be located on at least one of the moveable device 710, eyeglasses of a person in view of the moveable device, or anywhere the sensor 708 can sense the moveable device 710. The moveable device 710 can be, for example, a biopsy needle, a scalpel, a pathology wand, a locator wand, a bone segment, and the like.

Further comprising the exemplary system of FIG. 7 is a computing device 600, as described above. The computing device 600 receives the location information of the item of interest 704 from the device 702 and the position information of the moveable device 710 from the sensor 708 and executes computer-readable instructions that determine a relative position of the moveable device 710 to the item of interest 704 using the location information of the item of interest 704 from the device 702 and the position information of the moveable device 710 from the sensor 708, and provides feedback based on the relative position of the moveable device 710 to the item of interest 704 that can be used to change the relative position of the moveable device 710 to the item of interest 704. The computing device 600 can communicate with the sensor 708 and the device 702 using a network 712. The network 712 can comprise hardware and software. The computing device 600 can connect with the sensor 708 and the device 702 using wires (including fiber optic), wirelessly, or combinations of wired and wirelessly. In one aspect, the computing device 600 executes computer-readable instructions that cause the computing device 600 to provide audible feedback that is used to move the moveable device 710 closer to the item of interest 704. For example, the audible feedback may comprise computer-generated voice commands, computer-generated noises or haptic feedback that change as the moveable device 710 moves closer to or further away from the item of interest 704. Though not shown in FIG. 7, in one embodiment the system can further comprise a robotic surgical device, wherein the computing device 600 executes computer-readable instructions that cause the computing device 600 to provide a control signal that is used to provide robotic control of the moveable device 710.

Figure 8:
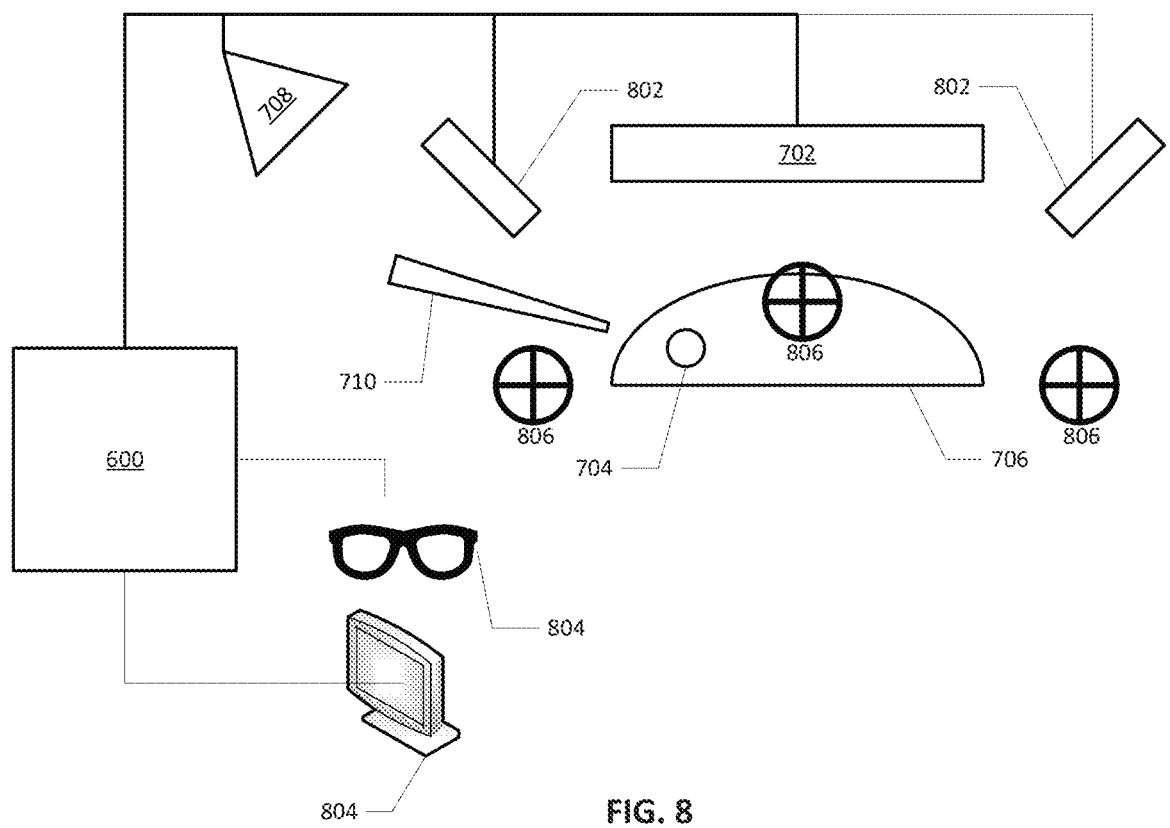
FIG. 8 illustrates another embodiment of a system for performing navigation-assisted medical procedures further comprising one or more cameras in communication with the computing device.

FIG. 8 illustrates an embodiment of a system for performing navigation-assisted medical procedures further comprising one or more cameras 802 in communication with the computing device 600. The one or more cameras 802 acquire a real-time image of the at least a portion of the subject 706, wherein the acquired real-time image is referenced to the same coordinate system as the location information of the item of interest 704 and the position information of the moveable device 710. In one embodiment, the system of FIG. 8 can further comprise a display 804 in communication with the computing device 600, wherein the real-time image of the at least a portion of the subject 706 is provided to the computing device 600 and the location information of the item of interest 704 and the position information of the moveable device 710 is super-imposed on the real-time image of the at least a portion of the subject 706 and displayed on the display 804. As shown in FIG. 8, in one aspect the display 804 can comprise augmented reality glasses. Embodiments of the system may further comprise one or more fiducials 806, wherein referencing the acquired real-time image to the same coordinate system as the location information of the item of interest 704 and the position information of the moveable device 710 is performed using the one or more fiducials 806 on or around the at least a portion of the subject 706. In one aspect, at least one of the one or more fiducials 806 can comprise a radioactive fiducial. In various aspects, the computing device 600 can provide feedback that indicates a depth that the moveable device 710 has been inserted into the item of interest 704. This can be done using audible feedback, visual feedback or a combination or audible and visual feedback.

The systems of FIGS. 7 and 8 enable re-registration of the item of interest 704. Re-registration comprises obtaining location information of the items of interest 704 either during or after a procedure involving the moveable device 710. Re-registration can be performed using the same devices and techniques as described in FIGS. 7 and 8 to initially determine the location of the item of interest 704. Re-registration may occur after movement of the item of interest 704, the at least a portion of the subject 706, or the subject, after removal of at least a portion of the item of interest 704 from the at least a portion of the subject 706, and the like. For example, if the item of interest 704 is cancerous tissue and the movable device is a scalpel, the surgeon may want to re-register the item of interest 704 after the initial surgical procedure to make sure that all of the cancerous tissue has been removed. In one aspect, re-registration occurs dynamically while the medical procedure is being performed.

EXAMPLES

A. Pathological Specimen Sampling

Pathologic staging of solid tumors involves determining the presence and extent of disease. Precise specimen processing is critical for establishing patient customized management plans that may indicate the need for post-operative chemotherapy and/or radiation therapy. Failure to identify malignant involvement in tissues can lead to the misdiagnosis and mismanagement of patients, leading to undesirable outcomes. Furthermore, correctly determining the extent of disease involves accurate assessment of the tumor's size, and the presence or absence of metastatic disease involving lymph nodes and distant tissues. Hence, the pathologist's assessment is crucial, and it plays a key role in basing future treatment options for patients.

Figure 9A:
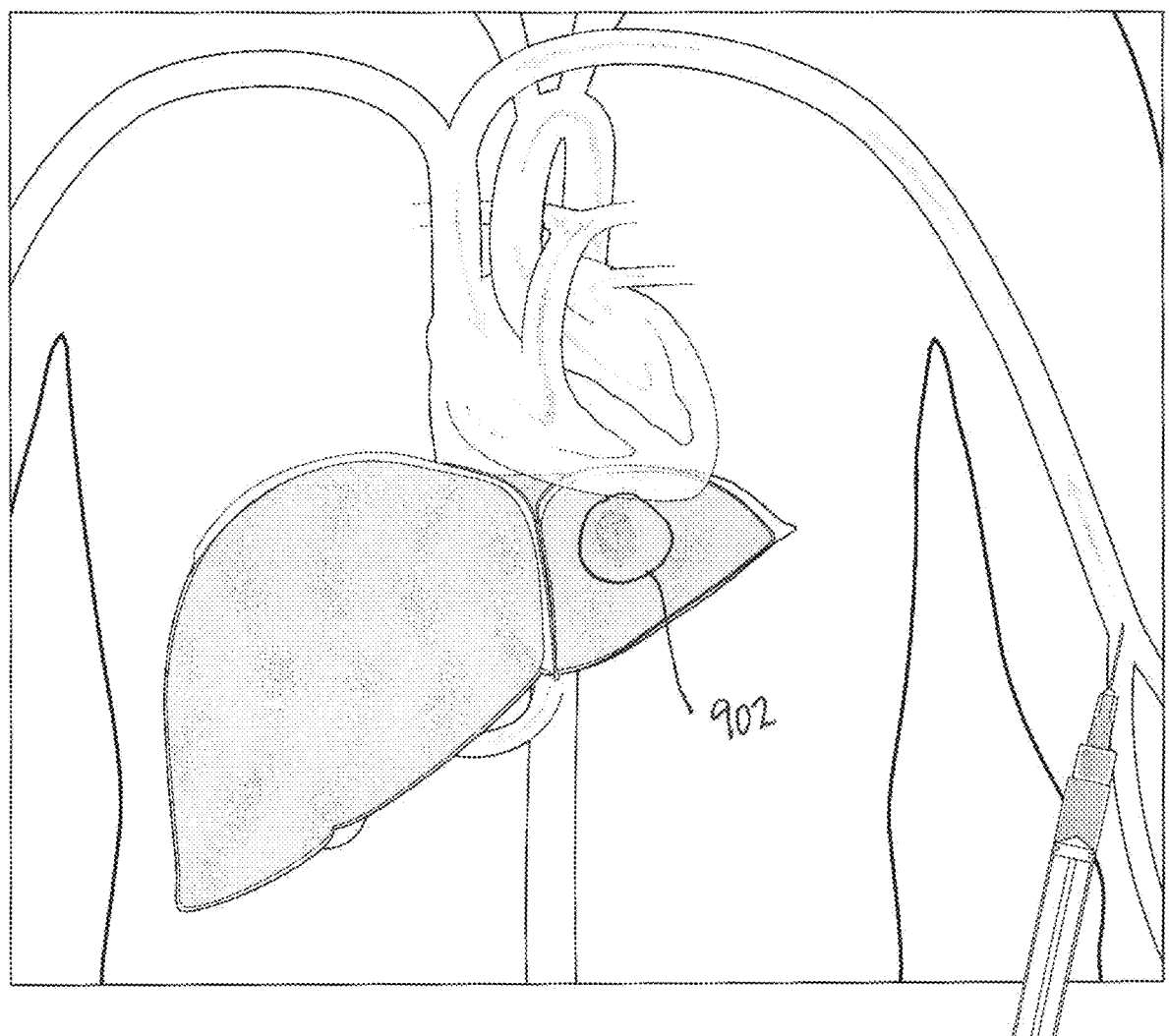
FIGS. 9A-9E illustrate an exemplary integrated process for targeted specimen analysis.
Figure 9B:
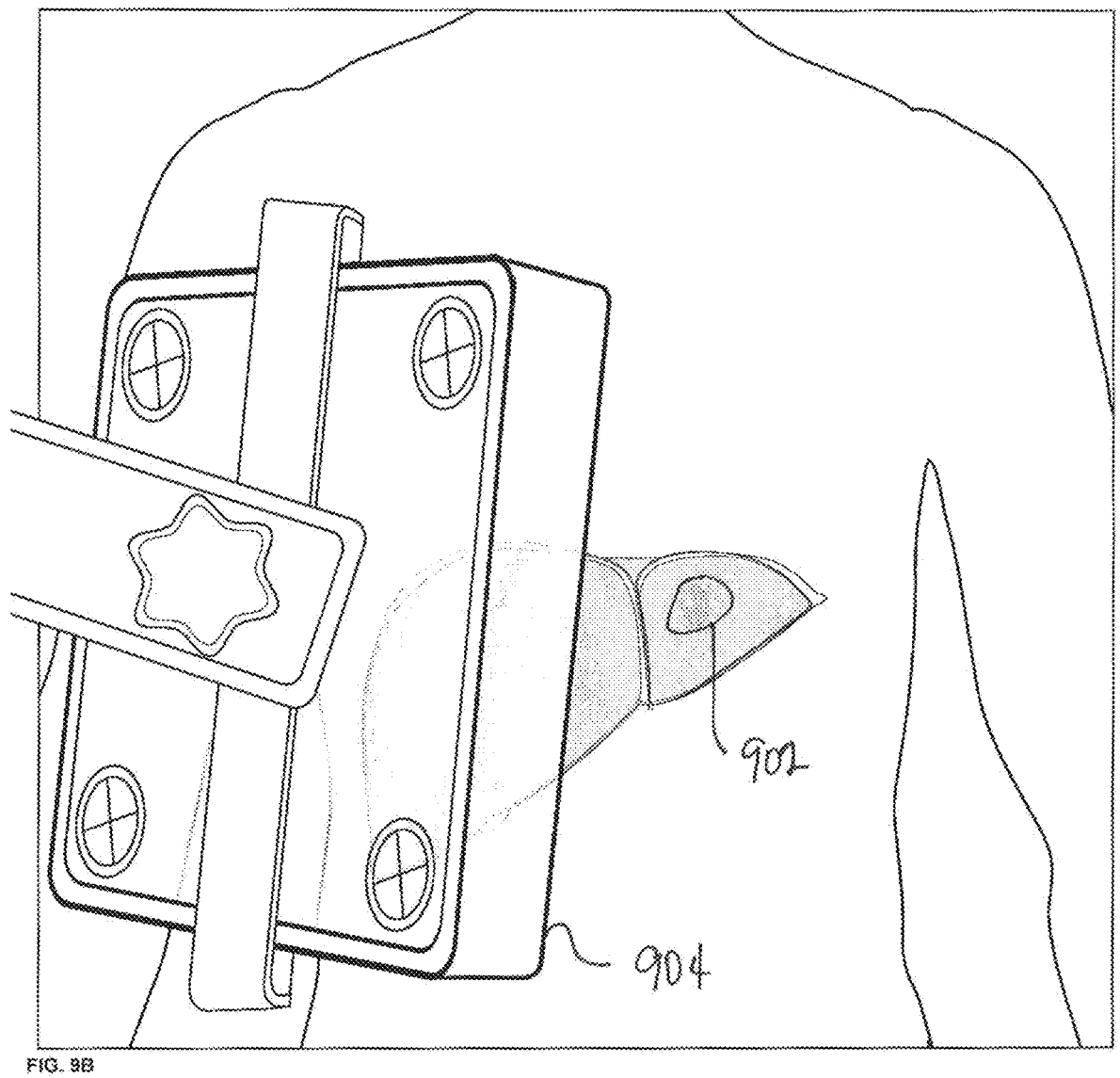
Figure 9C:
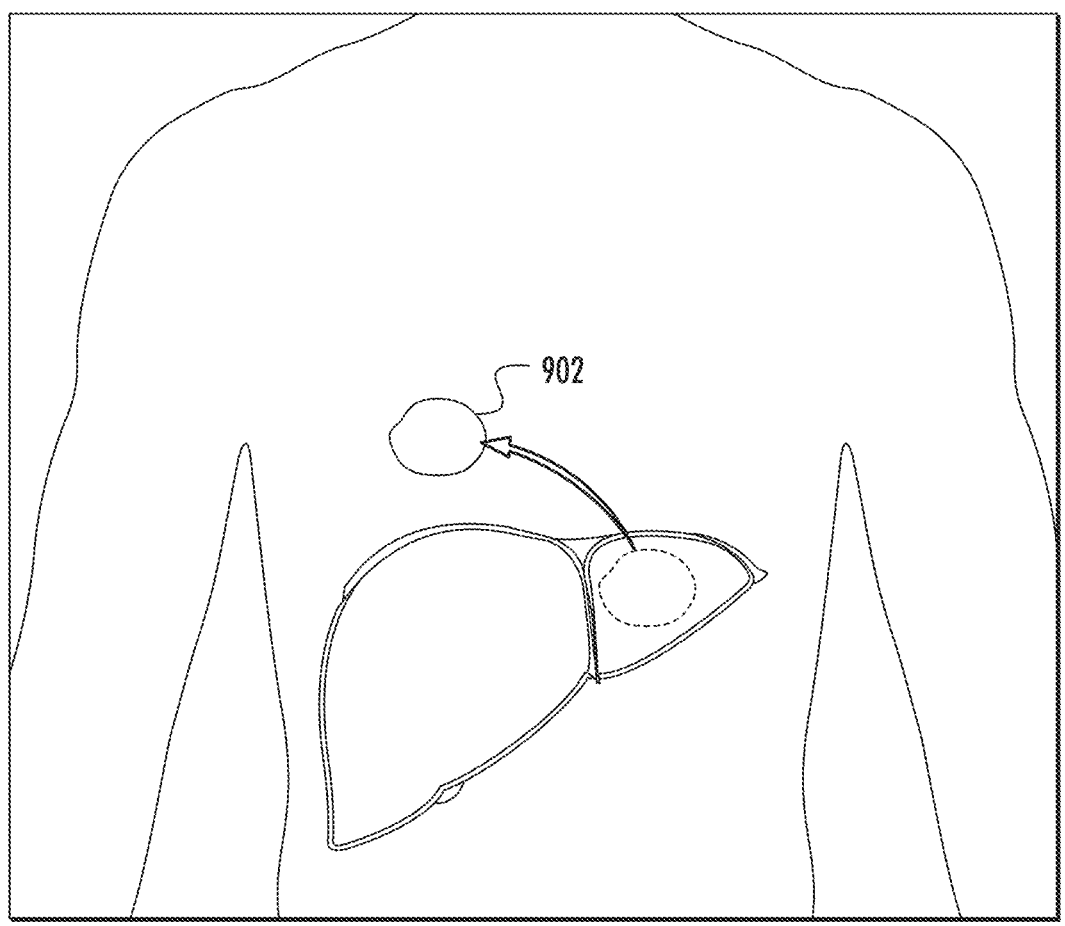
Figure 9D:
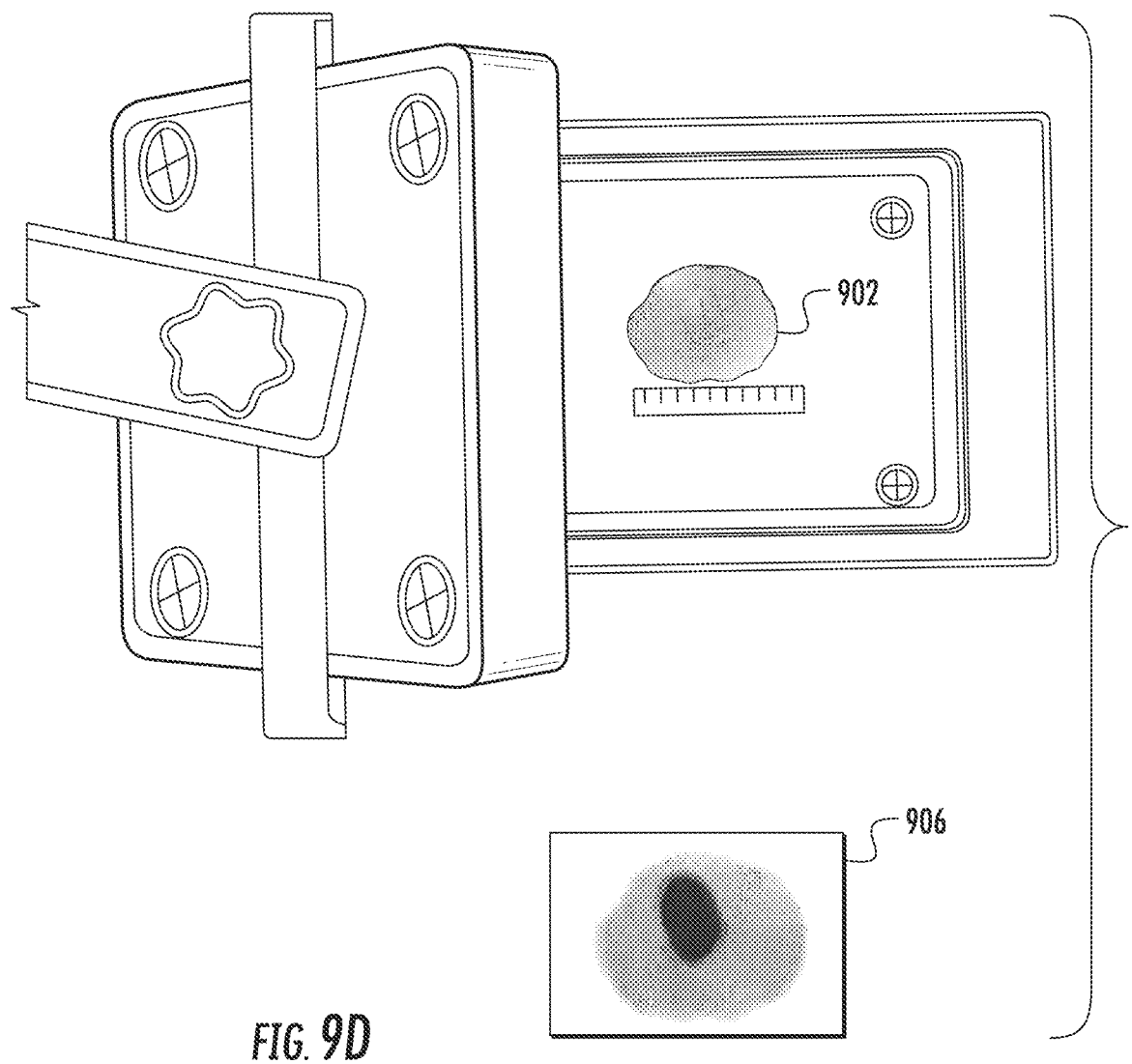
Figure 9E:
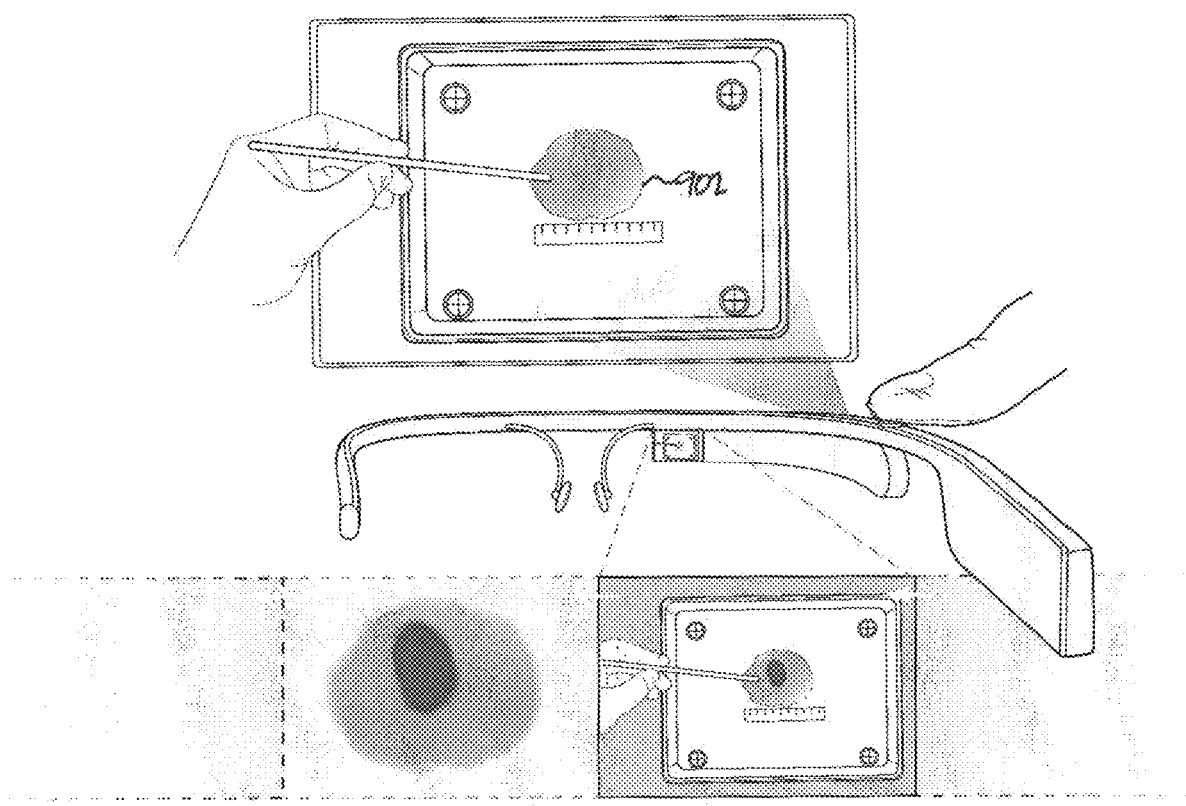

FIGS. 9A-9E illustrate an exemplary integrated process for targeted specimen 902 analysis. As shown in FIG. 9A, the tissue in this scenario is injected with a marker such as, for example, $^{99m}$Tc for nuclear imaging. In FIG. 9B, a device 904 such as, for example a portable gamma camera and planar lymphoscintigraphy are incorporated to permit 3D tumor localization in the specimen 902. After surgical resection (FIG. 9C), additional images 906 are taken of the specimen 902 (FIG. 9E). Utilizing augmented reality, 3D enhanced pathologic specimen sampling is performed for targeting the tumor as shown in FIG. 9E.

Embodiments of the system described herein provide an integrated system to improve the quality of analysis of the resected tumor specimen that provides the pathologist with the latest technological and scientific advancements. The developed system improves pathological detection efficiency and accuracy. It minimizes the occurrence of leaving tumors under-sampled, and thus reduces the incidence of misdiagnosis. The system is flexible in that it can be used for intra-operative margin assessment and postoperative specimen processing. Embodiments of the system provide image-guided cancer pathology by integrating a multi-camera tracking and navigation system with a portable Gamma Camera and SPECT/CT for low energy radio-isotopes and PET/CT imaging for high energy radio-isotopes. Images obtained can be used to generate an augmented visualization in a wearable product, such as Google Glass™, for guiding the pathologist by visualizing the location and extent of the cancerous tissue.

Currently, pathologists and pathologist's assistants (PA) rely on visual and tactile cues to identify and locate tumors and lymph nodes in resected tissue specimens. The process, or grossing, of a tissue specimen can be time consuming and is prone to sampling error. It has frequently been associated with "finding a needle in a haystack." Inaccurate processing of a tissue specimen may result in the incorrect pathologic staging being given. This can be the consequence of incomplete sampling of a lymph node, completely missing the tumor, or a failure to recognize the true relationship of the tumor to the closet margin of resection by sectioning the specimen in the wrong plane. Thus, it is highly desirable that the pathologist "can see" the cancer in its entirety in order to optimize treatment and offer the patient the best possible outcome.

Embodiments of the system described herein guide the pathologist/PA to where the tissue needs sampling. In cases of cancer of the head and neck, testes, prostate, melanoma, bladder, rectum, pancreas, stomach, and colon, accurate assessment of lymph nodes for metastatic disease is a must. Bringing the intra/postoperative images of the patient and the resected tissue to the pathologist's/PA's eye saves time while markedly increasing accuracy. The end result is improved treatment decision making.

A standard 2D image of a large specimen doesn't accurately reflect the number of tumors, their orientation, or their relationship to the nearest surgical margin of resection. Embodiments of the system described herein provide the pathologist/PA with a 3D view of the tumor(s) being targeted. This enables him/her with the ability to accurately identify and precisely sample the tissue, including the evaluation of the surgical margin of resection. This is especially useful in wide local excision of melanoma. Additionally, due to the technical advantages of this system, tissue sampling becomes more efficient and may provide intra-operative feedback to the surgeon in a manner that is more accurate than current intra-operative tissue analysis.

Figure 10A:
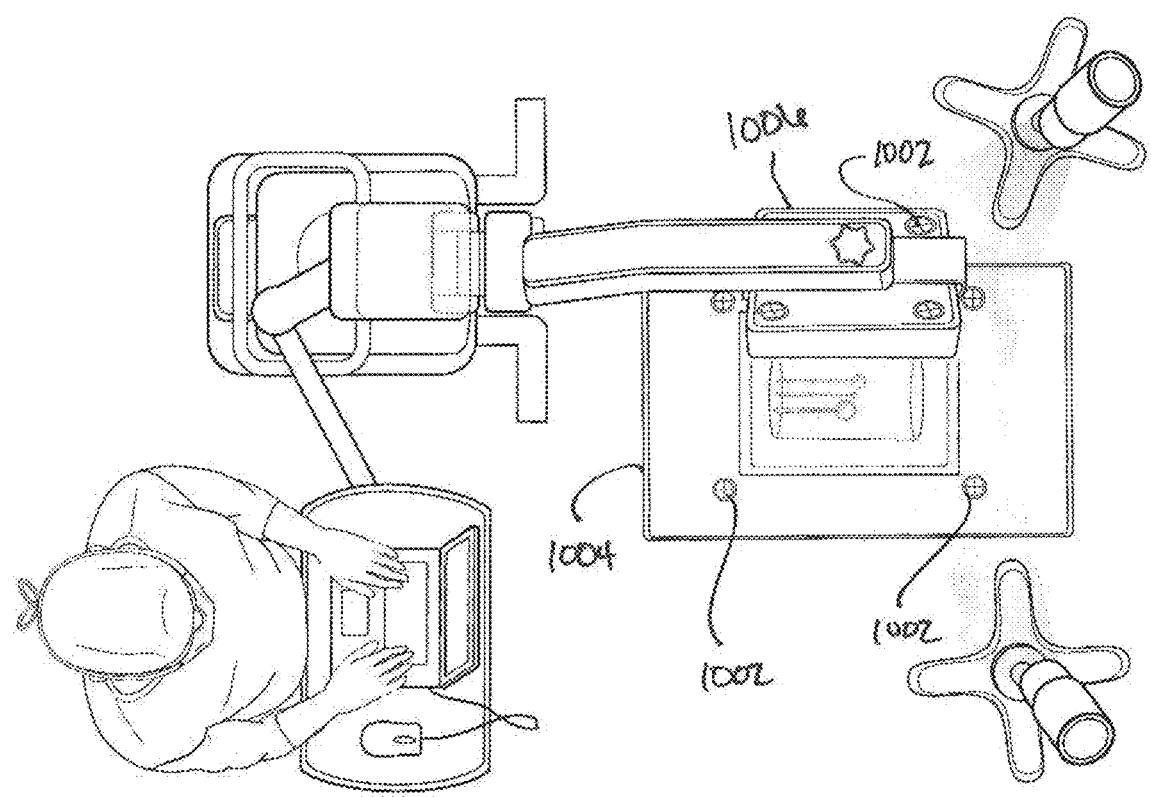
FIGS. 10A-10C illustrate a phantom bench top study used to show the accuracy of embodiments of the invention.
Figure 10B:
Figure 10C:
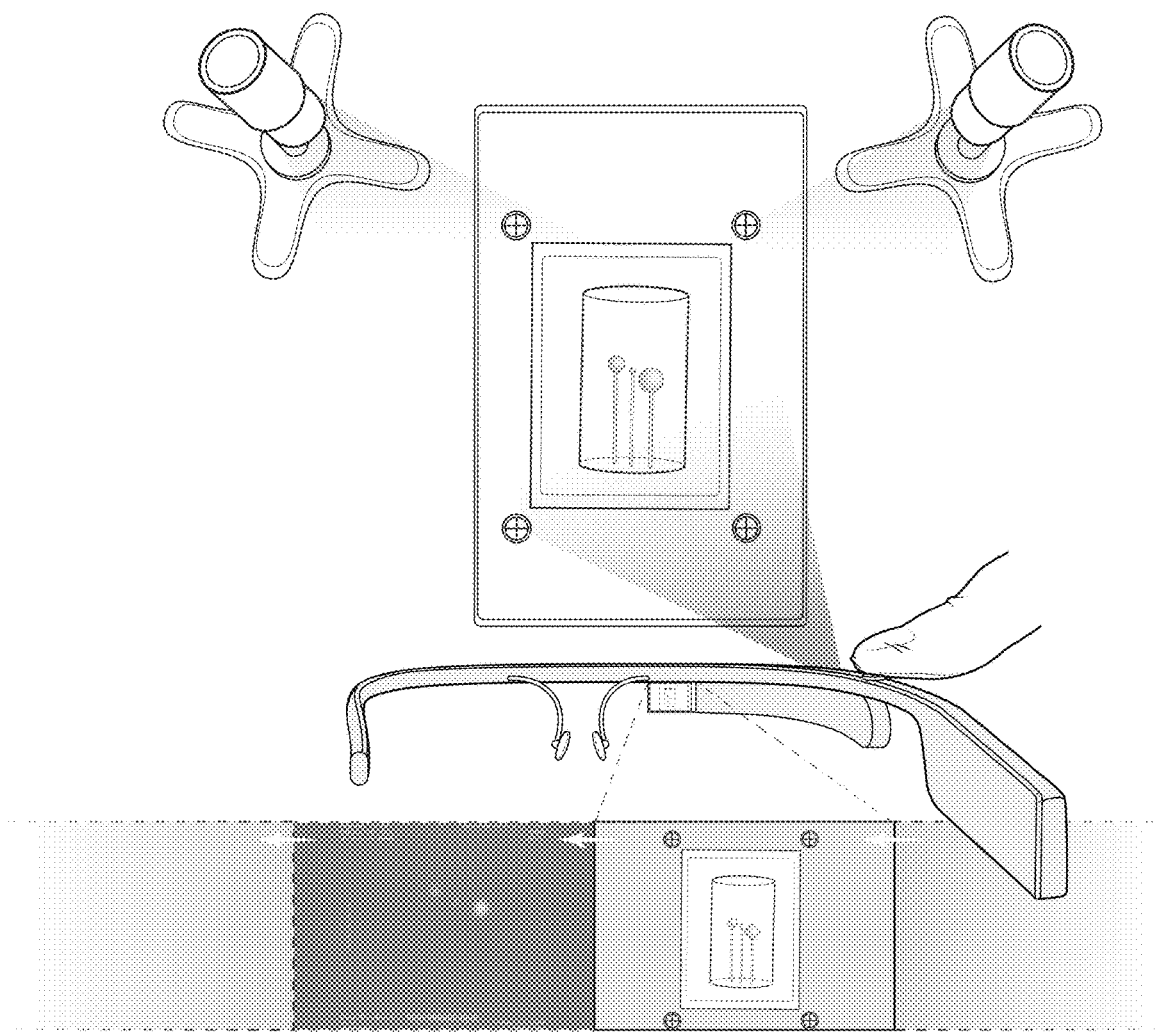

Described below is a non-limiting exemplary test of an embodiment of a system described herein. In FIG. 10A, a phantom bench top study is conducted with the fiducials 1002 placed on the phantom table 1004 and the gamma camera head 1006. FIG. 10B illustrates an exemplar gamma scan simulating breast sentinel node and head/neck sentinel nodes. FIG. 10C illustrates back-projected spheres (16 mL, 4 mL, and 1 mL) superimposed on one of the collected images, as seen through a moving camera. The three spheres, simulating separately sized tumors (1 mL, 4 mL and 16 mL), were injected with Technetium 99m and placed inside a glass phantom 1008. The glass phantom 1008 represents the entire resected specimen containing the foci, or spheres, of malignant disease. Fiducials 1002 were set around the phantom 1008 and on the gamma camera 1006 to recover the 3D geometry. Eight images were collected with the gamma camera from different viewing angles at 1.07" distance from the phantom. Results show successful recovery of the 3D sphere locations, as well as precise back-projections to the image acquired from a moving camera.

Figure 11:
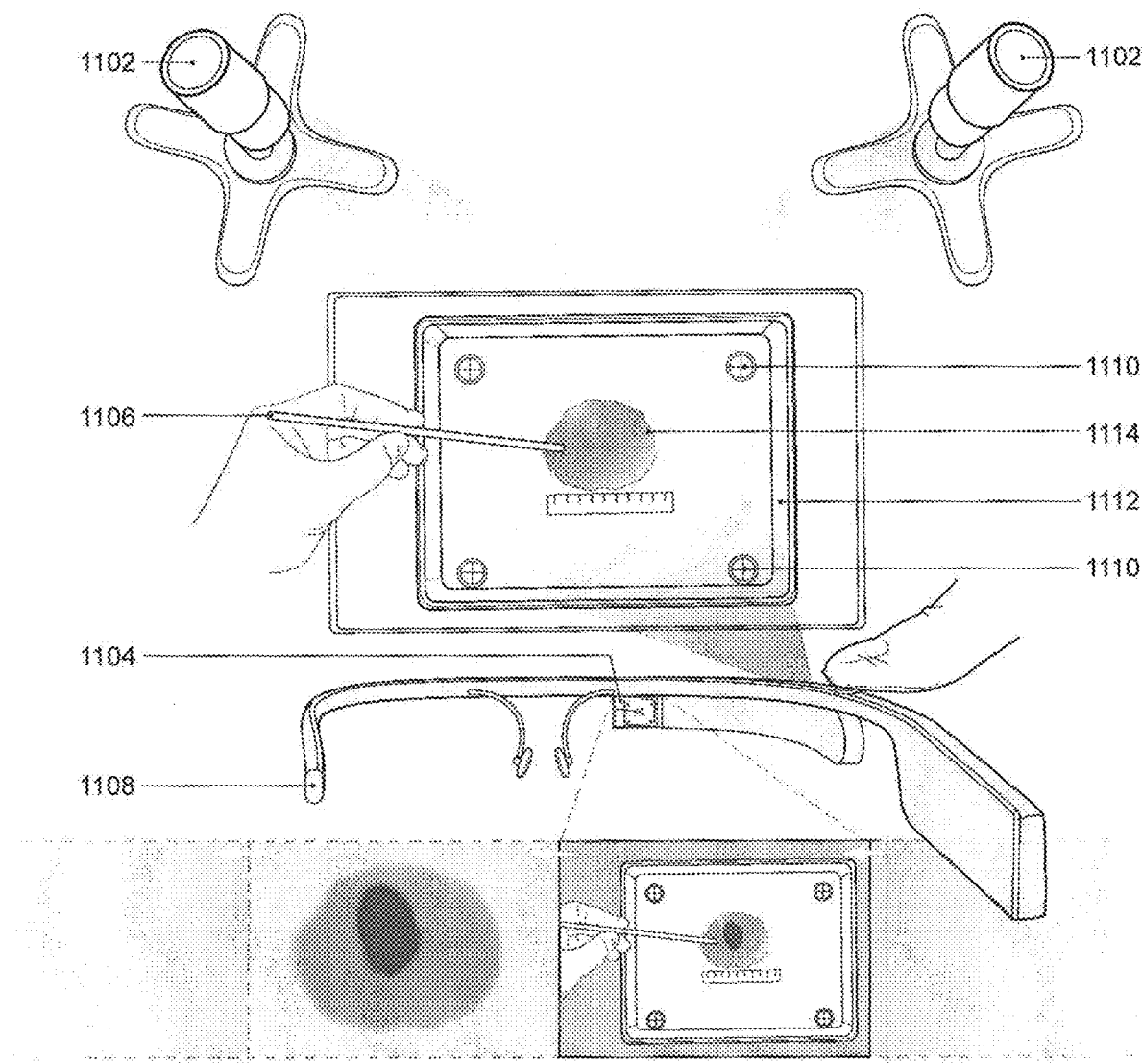
FIG. 11 illustrates one type of setup that can be used to perform aspects of embodiments of the invention.

FIG. 11 illustrates one type of setup that can be used to perform aspects of embodiments of the invention. In this setup, the proposed system is comprised of stereo electro-optical (EO) camera pair 1102 with overlapping field-of-views, medical imaging device 1104, a pathology locator wand 1106 and augmented reality glasses (e.g., Google Glass™) 1108, which can be worn by the pathologist. The EO cameras 1102 are used to detect and track a set of fiducials 1110 placed on the specimen tray 1112. The gamma camera, or other imaging modality 1104, provides the locations of lymphatic and cancerous tissues within the resected specimen 1114. In this setting, the augmented reality glasses 1108 can be used to generate an augmented reality by superimposing the location of the targeted tissues and the tip of the pathology locator wand 1106 onto the specimen 1114, as seen by the pathologist wearing the augmented reality glasses 1108. The wand 1106 can be used to pinpoint the targeted cancerous tissue inside the resected specimen 1114 and enable margin assessment quickly. A second proposed setup can generate the augmented reality by projecting the cancerous tumors onto the augmented reality glasses 1108 display without the use of the stereo camera pair 1102. This setting can provide visualization without the wand 1106. Regardless of the method used, upon removal of the targeted tumor(s) from the specimen 1114, the specimen 1114 can be reimaged to ensure precise removal of the targeted tumor(s) from the specimen 1114. In one aspect, the pathologist wearing the optics is able to point to the targeted tumor with the wand 1106 to within 1 mm of accuracy; thereby, ensuring accurate specimen 1114 processing. In one embodiment, distance indicators on the wand 1106 can be used to visually guide the pathologist.

In both of the above-described exemplary setups, each camera 1102 resides in their own reference frame and requires a referencing scheme to bring each of them into the same coordinate system. For pathology studies, two potential static reference frames that can be used include the stereo camera pair 1102 and the specimen tray 1112. In order to facilitate the referencing of all system components to a static reference frame, a shared set of radioactive fiducials 1110 can be placed on the tray 1112 that can be captured by the gamma camera image, augmented reality glasses 1108 and the stereo camera pair 1102 (if used). The initialization of the process starts with estimating the interior and exterior orientation parameters of the cameras prior to surgery, which will later be used for registration, detection and tracking purposes.

With the proper setup established, tissue analysis can be performed. Prior to the patient's operation, the patient can be injected intravenously with a nuclear isotope, such as Technetium 99. The isotope attaches to an antibody and the antibody, peptide and alike goes to the lymph nodes. While the tumor may not be directly detected or targeted as such, the potential location of the tumor and the isotope and its carrier can be injected around it for lymphatic mapping. The actual radio-isotope administered will be determined by the tumor type being targeted. During the surgery, the specimen(s) can be surgically resected following standard oncologic techniques. Once it has been removed from the patient, the tissue(s) can be placed on the specimen tray 1112 containing four or more embedded and shared fiducials 1110 at fixed positions that will be within the nuclear imaging field of view as mentioned above. The option for imaging modality includes, but is not limited to, the Gamma camera, SPECT/CT, PET/CT and micro SPECT/CT. The particular imaging method used for a given case can be guided by the particular radio-isotope administered. The 3D locations on the fiducials 1110 can be measured and registered to the augmented reality glasses 1108 camera and the EO stereo system 1102 (if used) by photogrammetric triangulation. The resected specimen containing the tumor(s), and accumulated isotope within can be visualized on the acquired images from a minimum of two different orientations with a baseline between acquisition positions. Using a pre-established model that adopts orthographic and para-perspective projections, the 3D positions of the targeted tissues can be estimated through the same process used in computing the 3D positions of shared fiducials.

A statistical software package can be used to analyze all the bench top and vivo data. The bench top measurements are expressed as mean±standard deviation. The in vivo data can be analyzed using one-way analysis of variance (ANOVA) method, with the differences among the means evaluated by the Tukey-Kramer multiple comparison test. A P-value of less than 0.05 is considered statistically significant.

B. Image-Guided Cancer Surgery

Historically, surgery has offered the best opportunity for cure in patients with solid malignancies. Previous optimal surgical approach to cancer resection was limited to visual and tactile cues in identifying the tumor's location and extent. Operations were based on surgical anatomy and traditional planes of resection that cancer cells frequently disregarded. Thus, it became evident that the a challenge to cancer surgery is for the surgical team "see" all of the tumor(s), including metastases, to achieve the best resection and offer the patient the best possible outcome. Since the early 1990s, this concept has materialized by the incorporation of preoperative imaging, such as PET/CT and SPECT/CT. However, these imaging techniques do not provide a real-time intra-operative assessment of tumor location or to indicate whether the malignancy has been completely resected.

Described herein are embodiments of an integrated system for real-time intra-operative tumor tracking and surgical guidance. Embodiments of this invention deliver better science to the surgeon before, during and after the surgery to help locate primary and metastatic tumors, guide complete excision of malignant tissues in a single surgery, and assess completeness of resection. As a result, cost-effective and personalized patient care, with improved outcomes, will be achieved while reducing the chance of leaving residual tissue behind. One embodiment of the system integrates multi-camera tracking and navigation system with intraoperative portable gamma camera scans for generating augmented visualization for surgical guidance until no residual cancer remains.

Figure 12A:
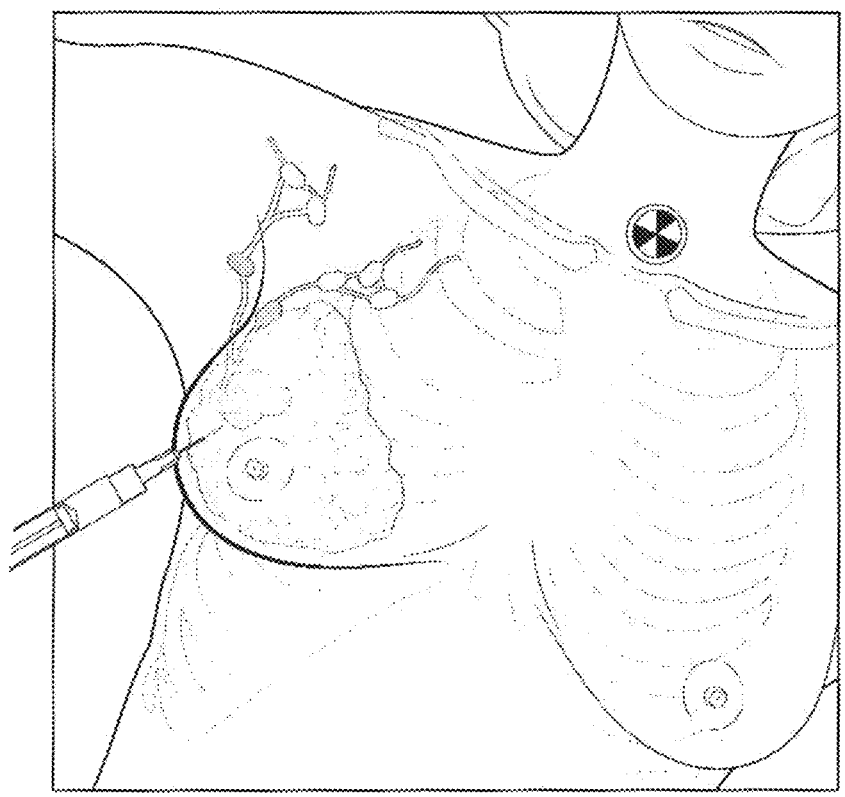
FIGS. 12A-12H illustrate an integrated methodology and schema for image-guided cancer surgery.
Figure 12B:
Figure 12C:
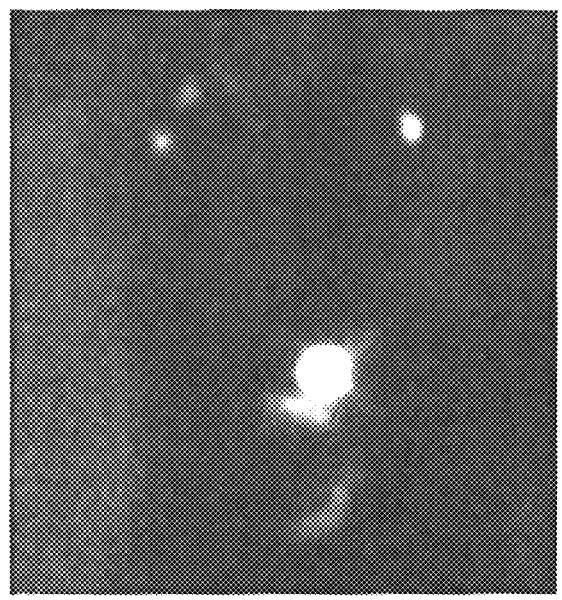
Figure 12D:
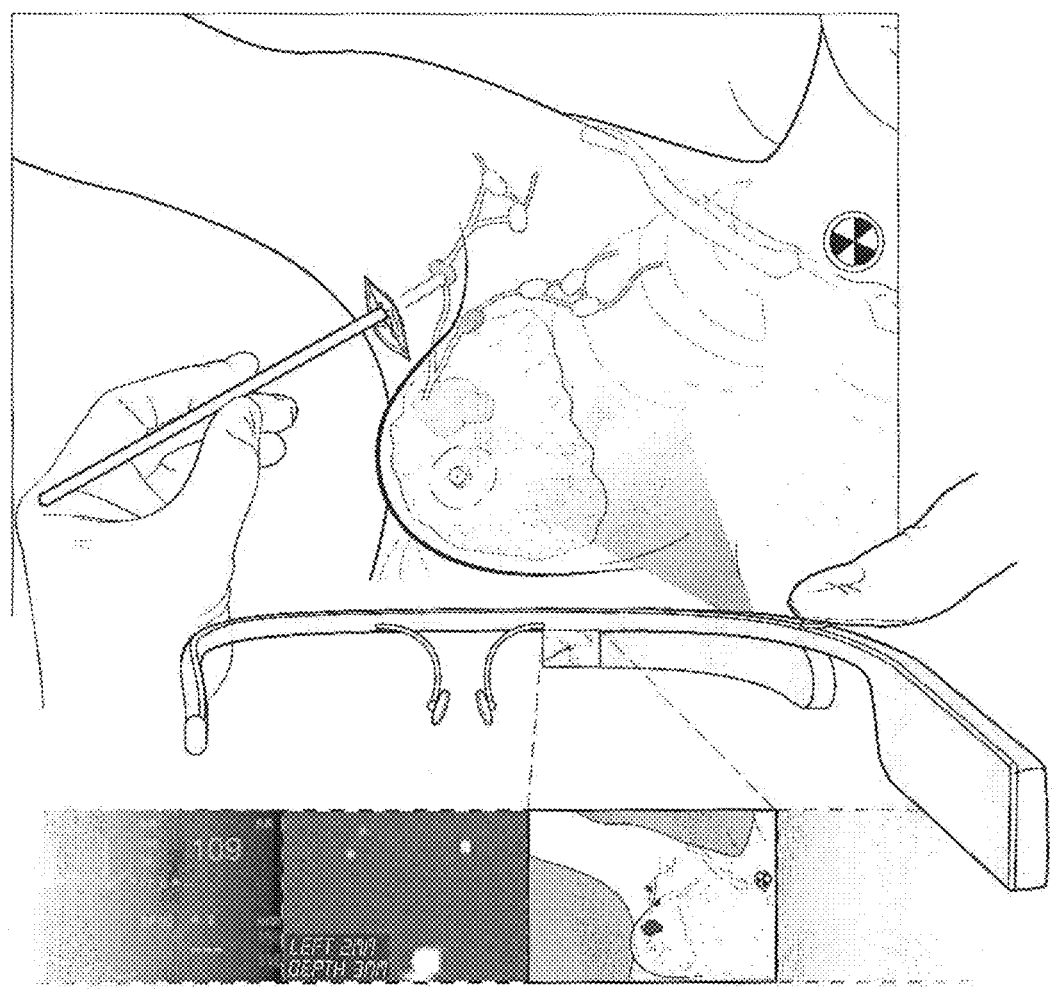
Figure 12E:
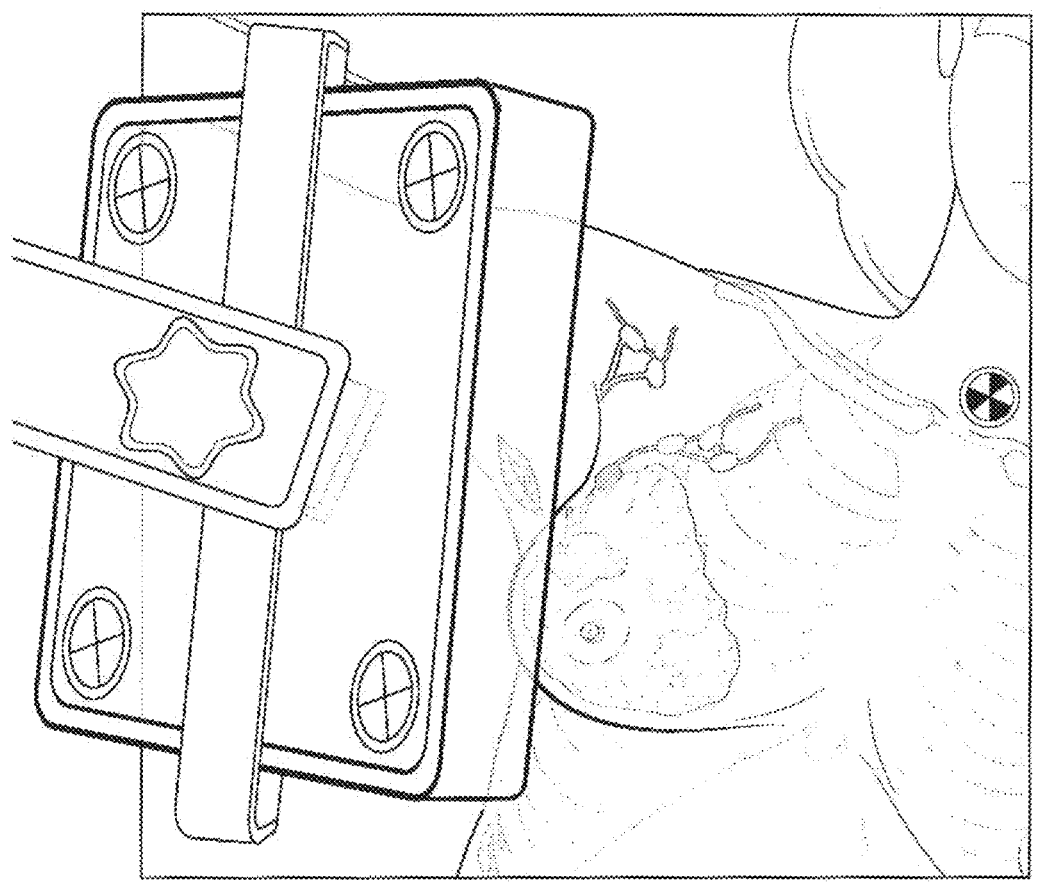
Figure 12F:
Figure 12G:
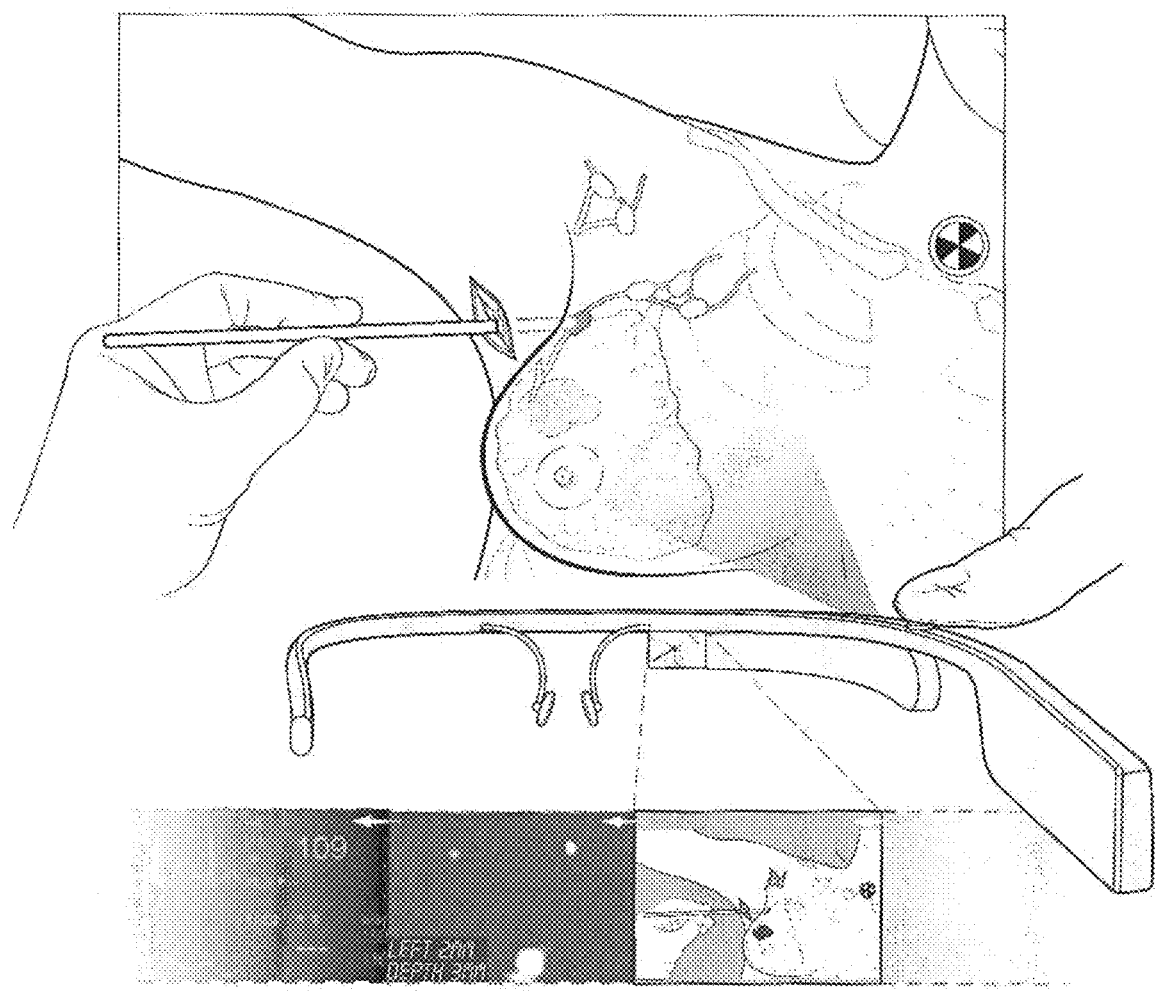
Figure 12H:

FIGS. 12A-12H illustrate an integrated methodology and schema for image-guided cancer surgery. In FIG. 12A, the tissue is injected with, for example, $^{99m}$Tc for intra-operative imaging. In FIGS. 12B and 12C, preoperative gamma camera is incorporated for 3D lymphatic mapping, which in FIG. 12D, is projected onto augmented reality glasses (e.g., Google Glass™) for surgical guidance. As shown in FIGS. 12E-12H, additional gamma camera images are scanned and residual cancerous tissue is resected until the cancer has been completely removed.

Accurate assessment of the extent of disease is the cornerstone to minimizing cancer recurrence rates and ultimately translates into improved overall outcomes. While significant advances have occurred in the last two decades, cancer imaging is still primarily focused on preoperative image acquisition. Currently, the only intra-operative surgical tool that provides real-time cancer-specific information is the hand-held gamma probe. However, it does not provide information regarding tumor margins. Furthermore, localizing small tumors with the probe may take a significant amount of time due to the difficulty in directing the probe with respect to the preoperative images. Therefore, embodiments of the system described herein provide real-time surgical guidance system for tumor delineation, lymphatic mapping, and for navigating the surgeon to missed residual tumor foci for resection during the initial operation. This can lead to fewer reoperations and improved surgical cure rates, which can be up to 20% in breast cancer.

Figure 13:
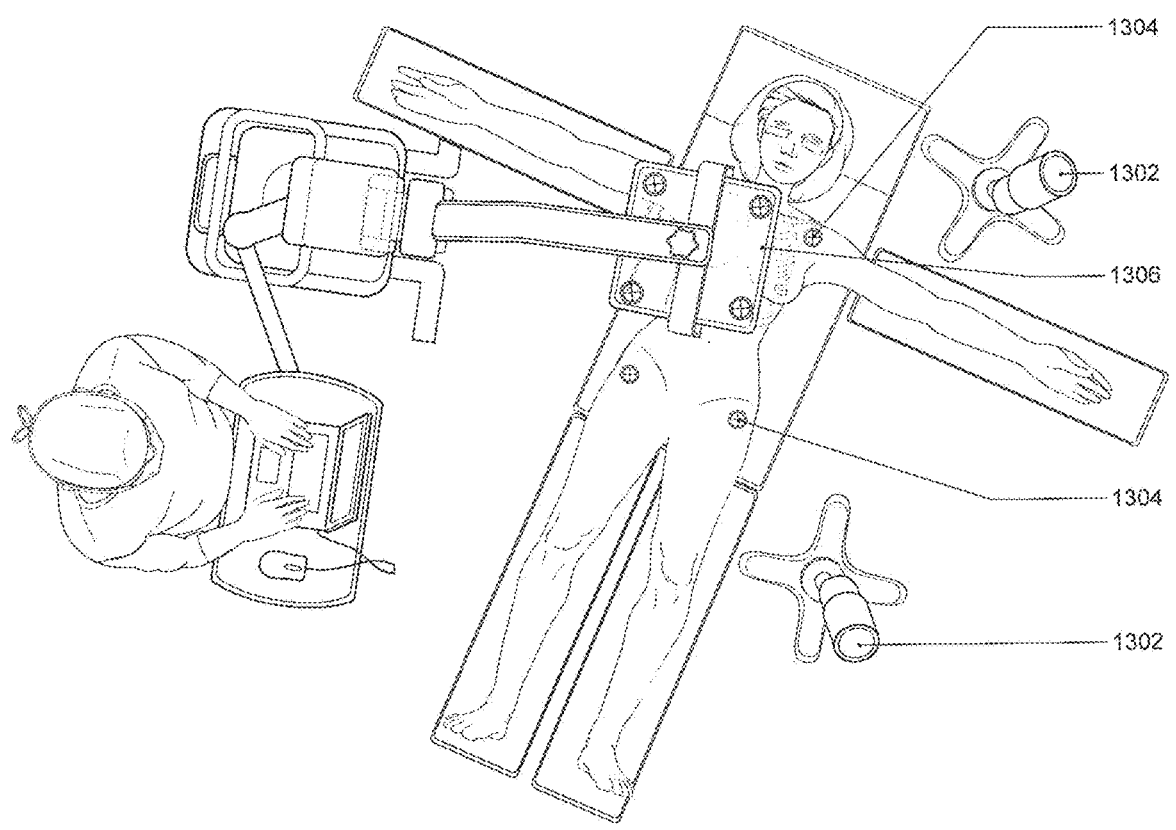
FIG. 13 illustrates an embodiment of a system for operating room (OR) setup for intra-operative imaging and 3D recovery and tracking.

FIG. 13 illustrates an embodiment of a system for operating room (OR) setup for intra-operative imaging and 3D recovery and tracking. This embodiment is comprised of stereo electro-optical (EO) cameras 1302 with overlapping field-of-views, one gamma camera 1306 and a display or augmented reality glasses worn by the surgeon (not shown FIG. 13). The EO cameras 1302 are used to detect and track a set of fiducials 1304 on the patient and surgeon; the gamma camera 1306 provides the locations of the targeted tissue, and the display or augmented reality glasses are used to generate augmented reality by projecting these regions onto the surgical scene as seen by the surgeon. Each one of these cameras resides in their own reference frame and requires an explicit referencing scheme that will bring them into the same frame. One stationary component of the setup that can be used to establish the reference frame is the stereo camera 1302; therefore, all imaging devices can be referenced to the stereo system 1302. In order to facilitate this referencing, a shared set of radioactive fiducials 1304 can be placed on the patient only at the time of gamma scanning, and they will be captured in both the gamma camera image and the stereo system images. The initialization of the surgical process starts with estimating the interior and exterior orientation parameters of the stereo cameras prior to surgery and will later be used for registration, detection and tracking purposes.

Prior to preoperative gamma camera imaging, a plurality (e.g., four) shared fiducials 1304 are placed on or near the patient at positions that are within the gamma camera's 1306 field-of-view. The 3D locations on the fiducials 1304 are registered to the stereo system 1302 by photogrammetric triangulation that estimates (X, Y, Z) of the fiducials 1304 by a bundle adjustment process. The gamma scans of the tissue exposed to the Technetium 99m can then be acquired from a minimum of two different orientations with some baseline between acquisition positions. Using a pre-established gamma camera model that adopts orthographic projection, the 3D centers of the targeted tissues can be estimated through the same process used in computing the 3D positions of the shared fiducials 1006. In order to establish a model for delineating the margin of resection for suspected cancers, the gamma camera 1306 image typically provides different margins at different contrast levels. In order for the surgeon to plan a safe margin of resection around the tumor, a maximum contrast level is used and the entire set of pixels within the margin from all acquired images is back-projected, which will generate a 3D volume. This can then be modeled by radon transform or convex hull that can be used for generating augmented reality. For computational efficiency, volumetric methods with voxel size adjusted according to the gamma camera pixel size are adopted. As noted above with reference to FIGS. 10A-10C, a successful benchtop study has been conducted to prove the localization and back projection concept introduced above.

At times, multiple tumors will be present and one, or more, may be obstructed or hidden behind a more superficial tumor, which may lead to residual cancer left behind if not identified. One approach is to use a surgical wand, such as a suction tip, to guide the surgeon to such cancerous tissues prior to completing the surgery. This guidance allows the surgeon to perform a secondary check with the hand-held gamma probe to locate and make sure that the tissue is truly involved. In order to achieve this, the stereo camera system detects and tracks a set of fiducials mounted onto the wand in real-time to estimate its tip position and orientation. One possible arrangement is to place one of the fiducials on the wand base and the other towards the tip of the wand to define a 3D line for tracking purposes. Another arrangement is to organize four fiducials on a planar patch mounted onto the base of the wand.

Prior to the operation, the relative positions of the fiducials can be registered to the tip of the wand by the stereo system for accurate position and orientation estimation. The system detects and tracks the fiducials by performing kernel-tracking algorithms modified by introducing geometric constraints to improve geometric localization. In addition, spatiotemporal constraints are used to reduce the computational time and increase precision. The spatiotemporal constraints are incorporated into the detection and tracking framework in the form of Markov Random Fields applied to a stack of consecutive frames generating Markov Random Volumes. Upon tracking the positions, the orientation and the wand tip position can be estimated by intersecting tracked locations from stereo-cameras by bundle adjustment. Once the tip is located, the surgeon will have visual and auditory guidance that will include verbal directions to move the wand tip towards the target tissue. The auditory signals are referenced to the wand tip and are in the form of directional information, such as "left" and "right", and distance information.

Visual feedback can be generated by back-projecting the 3D locations of the target tissues and the wand tip to an augmented reality display interface (e.g., Google Glass™). The back-projection requires registering the 3D position and orientation of the augmented reality display interface to the stereo camera reference frame. This registration requires real-time tracking of the augmented reality display interface in stereo image pair. For achieving high precision in augmented reality display interface tracking, a set of fiducials can be mounted on a surgical head-band worn by the surgeon, and recover relative geometry between them by triangulating matching fiducials. This process can be performed before the operation when the surgeon puts the head-band and augmented reality display interface on. In order to assist augmented reality display interface tracking, additional sensory data that the augmented reality display interface (e.g., Google Glass™) provides, such as magnetometer and inertial measurements can be used. These measurements will serve as initial orientation information for iterative orientation estimation. Upon recovering the augmented reality display interface (e.g., Google Glass™) orientation, the 3D positions of wand tip and the target tissues, i.e. parathyroid adenomas, can be back-projected to the augmented reality display interface (e.g., Google Glass™) camera display unit to create an augmented reality that adjusts to the surgeons viewing angle to correctly resect the target tissue. The gamma scanning, 3D localization and tracking followed by tumor resection can be iterated as many times as necessary until no residual tissue is left.

Figure 14:
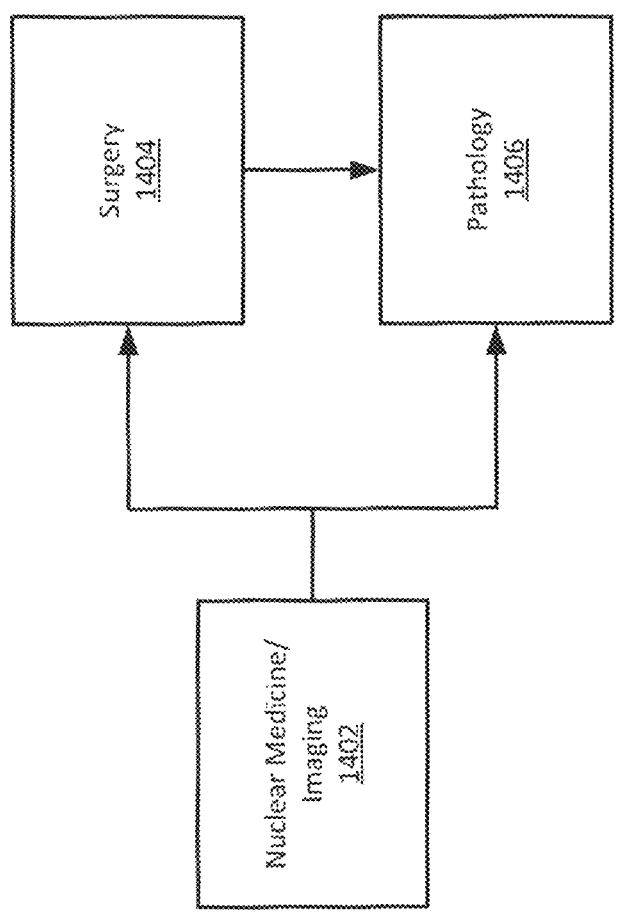
FIG. 14 is an exemplary flow diagram that illustrates the integrated nature and use of embodiments of the present invention in a medical application.

FIG. 14 is an exemplary flow diagram that illustrates the integrated nature and use of embodiments of the present invention in a medical application. For example, a 3D model of an item of interest can be created in nuclear medicine/imaging 1402 using devices and techniques as described herein. The model created in nuclear medicine/imaging 1402 can be used in surgery 1404 or pathology 1406 by a professional to better see the item of interest and to determine it margins or alignment. Overall, the embodiments of systems and methods described herein provide a better tool for the medical professional and a better medical experience for the patient.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:
1. A method of performing navigation-assisted medical procedures comprising:
  estimating location information of an item of interest located within at least a portion of a subject using an algorithmic deformation model based on acquired image information to estimate unobserved motion of the item of interest within at least the portion of the subject;

sensing position information of a moveable device;

determining a relative position of the moveable device to the item of interest using the estimated location information of the item of interest and the position information of the moveable device; and providing directional and distance active feedback based on the relative position of the moveable device to the item of interest that can be used to change the relative position of the moveable device to the item of interest during a navigation-assisted medical procedure, wherein the active feedback changes as the moveable device moves closer to or further away from the item of interest, and wherein the distance active feedback comprises distance encoded vibration frequencies provided through the moveable device.

2. The method of claim 1, wherein estimating location information of the item of interest comprises obtaining an image of at least a portion of the item of interest.

3. The method of claim 1, wherein estimating location information of an item of interest located within at least a portion of a subject comprises estimating location information of a tumor within at least a portion of a subject, cancerous tissue within at least a portion of a subject, or an organ within a body of the subject.

4. The method of claim 1, wherein estimating location information of an item of interest located within at least a portion of a subject comprises estimating location information of the item of interest within a body of the subject, estimating location information of the item of interest within an organ of the subject, or estimating location information of the item of interest within a tissue specimen.

5. The method of claim 1, further comprising inserting the moveable device into the item of interest, wherein the feedback indicates a depth that the moveable device has been inserted into the item of interest.

6. The method of claim 1, wherein providing feedback based on the relative position of the moveable device to the item of interest that can be used to change the relative position of the moveable device to the item of interest further comprises:

acquiring a real-time image of the at least a portion of the subject, wherein the acquired real-time image is referenced to the same coordinate system as the location information of the item of interest and the position information of the moveable device; and displaying the real-time image of the at least a portion of the subject further comprising the estimated location information of the item of interest and the position information of the moveable device super-imposed on the real-time image of the at least a portion of the subject.

7. The method of claim 1, wherein providing feedback based on the relative position of the moveable device to the item of interest that can be used to change the relative position of the moveable device to the item of interest comprises providing one or more of visual, audible or haptic feedback that is used to move the moveable device closer to the item of interest.

8. The method of claim 1, wherein providing feedback based on the relative position of the moveable device to the item of interest that can be used to change the relative position of the moveable device to the item of interest comprises providing a control signal that is used to provide robotic control of the moveable device.

9. The method of claim 1, wherein sensing position information of the moveable device comprises actively or passively sensing position information of a biopsy needle, a scalpel, a pathology wand, a locator wand, or a bone segment.

10. The method of claim 1, wherein sensing position information of the moveable device comprises obtaining position information of the moveable device using a three-dimensional sensor.

11. The method of claim 1, wherein determining the relative position of the moveable device to the item of interest using the estimated location information of the item of interest and the position information of the moveable device is performed using a computing device.

12. The method of claim 1, further comprising re-registration of the estimated location information of the item of interest located within at least a portion of a subject.

13. The method of claim 1, further comprising estimating movement or deformation of the item of interest caused by movement or palpation of the at least a portion of the subject, wherein the estimated location information of the item of interest is modified by the estimated movement or deformation of the item of interest.

* * * * *